United States Patent [19]

Bishop et al.

[11] Patent Number: 5,876,962
[45] Date of Patent: Mar. 2, 1999

[54] EXPRESSION VECTORS FOR THE SYNTHESIS OF PROTEINS AND PLASMID REPLICONS AND SEQUENCE CASSETTES FOR USE IN CONSTRUCTING SUCH VECTORS

[75] Inventors: David H.L. Bishop, Oxford; Vincent Clive Emery, Nightingale, both of United Kingdom

[73] Assignee: Natural Environment Research Council, Oxford, United Kingdom

[21] Appl. No.: 486,101

[22] Filed: Jun. 7, 1995

Related U.S. Application Data

[63] Continuation-in-part of Ser. No. 423,302, Apr. 18, 1995, abandoned, which is a continuation of Ser. No. 245,512, May 11, 1994, abandoned, which is a continuation of Ser. No. 102,549, Aug. 5, 1993, abandoned, which is a continuation of Ser. No. 940,759, Sep. 8, 1992, abandoned, which is a continuation of Ser. No. 346,942, filed as PCT/GB88/00663, Aug. 11, 1988, abandoned.

[30] Foreign Application Priority Data

Aug. 12, 1987 [GB] United Kingdom ............... 8719108

[51] Int. Cl.⁶ .................................................. C12P 21/06
[52] U.S. Cl. .................... 435/69.1; 435/70.1; 435/172.3; 435/320.1; 435/348
[58] Field of Search ............................. 435/69.1, 69.7, 435/172.3, 172.1, 320.1, 348; 536/24.1, 24.2; 935/23, 32, 70

[56] References Cited

U.S. PATENT DOCUMENTS

| | | | |
|---|---|---|---|
| 4,713,339 | 12/1987 | Levinson et al. | 435/240.2 |
| 4,745,051 | 5/1988 | Smith et al. | 435/68 |
| 4,870,023 | 9/1989 | Fraser et al. | 435/320.1 |
| 4,879,236 | 11/1989 | Smith et al. | 435/235 |
| 5,169,784 | 12/1992 | Summers et al. | 435/320.1 |

FOREIGN PATENT DOCUMENTS

| | | | |
|---|---|---|---|
| 0127 839 A2 | 12/1984 | European Pat. Off. | C12N 15/100 |
| 0 327 626 B1 | 11/1988 | European Pat. Off. | C12N 15/100 |
| WO 89/01518 | 2/1989 | WIPO | C12N 15/00 |

OTHER PUBLICATIONS

Garrity, David B. et al., Late Promoter Selection in the Baculovirus gp64 Envelope Fusion Protein Gene, *Virology*, 231, 167–181, 1997.

O'Reilly, David R., et al., Gene Organization, Regulation, and Function, *Baculovirus Expression Vectors, A Laboratory Manual*, 12–23, 1994.

Carbonell, Luis F., Klowden, Marc J., and Miller, Lois K., Baculovirus Mediated Expression of Bacterial Genes in Dipteran and Mammalian Cells; *Journal of Virology*, 56:153–160, 1985.

Belyeav AS, Hails RS, and Roy P (1995). High–level expression of five foreign genes by a single recombinant bacuiovirus. Gene, 156:229–233 (1995).

Belyaev AS, and Roy P. (1992). Presentation of Hepatits B Virus preS₂ Epitope on Bluetongue Virus Core–like Particles. Virology 190:840–844.

Belyaev A.S., and Roy P. (1993). Development of baculovirus triple and quadruple expression vectors: co–expression of three or four bluetongue virus proteins and the synthesis of bluetongue virus–like particles in insect cells. Nucleic Acids Research 21(5):1219–1223.

Bishop, D.H.L. (1994). Baculoviruses and Baculovirus Expression Systems: Use in Expression of Proteins. Methods in Molecular Genetics 4:253–281.

Bishop, D.H.L. (1992). Baculovirus expression vectors. Virology 3:253–264.

Bishop D.H.L., Hill–Perkins, M., Takehara, K., Urakawa, T., Weyer U., and Possee, R. D. The development and use of baculovirus vectors for multigene expression. Recombinant Systems I–Foreign Expression, K. Aliko M. Muhtak, J. Knowles and A. Vaheri, Eds. pp. 56–61, Elsevier, Amsterdam.

Cory, J.S., Hirst, M.L., Williams, T., Hails, R.S., Goulson, D., Green, B.M., Carty, T.M., Possee, R.D. Cayley, P.J., and Bishop, D.H.L. (1994). Field trial of a genetically improved baculovirus insecticide. Nature 370:138–140.

Emery, V.C., and Bishop, D.H.L. (1987). The develpment of multi expression vectors for high level synthesis of eukaryotic proteins: expression of LCMV–N and AcNPV polyhedrin protein by recombinant baculovirus. Protein Engineering 1(4):359–366.

French, T.J., Marshall, J.J.A., and Roy, P. (1990). Assembly of double–shelled, virus–like particles of bluetongue virus by the simultaneous expression of four structural proteins. Journal of Virology 64(12): 5695–5700.

(List continued on next page.)

*Primary Examiner*—James Ketter
*Assistant Examiner*—Iran Yucel

[57] ABSTRACT

Expression vectors for the expression of proteins, particularly eukaryotic proteins are provided which are based on novel plasmid replicons. Sequence cassettes useful in constructing such vectors are also disclosed. The expression vectors according to the invention are useful for expressing selected proteins in insects and insect cells. Specifically, the plasmid replicons comprise double-stranded DNA having (a) one or more sequences allowing the replicon to be reproduced in a bacterial host, (b) first and second sequences which are adapted to permit an intervening sequence located between said first and second sequences to be introduced into an expression vector, and (c) an intervening sequence located between said first and second sequences, and are characterised in that the intervening sequence comprises first and second polypeptide expression sequences (PESs) wherein each PES includes (i) a transcriptional promotor (ii) a unique restriction site for introduction of a gene which is native or foreign to the expression vector and (iii) a transcriptional termination site.

29 Claims, 23 Drawing Sheets

OTHER PUBLICATIONS

French, T.J. and Roy, P. (1990). Synthesis of bluetongue virus (BTV) core–like particles by a recombinant baculovirus expressing the two major structural core proteins of BTV. Journal of Virology 64(4):1530–1536.

Hewat, E.A., Booth, T.F., Loudon, P.T., and Roy, P. (1992). Three–dimensional reconstruction of baculovirus expressed bluetongue virus core–like particles of cryo–electron microscopy. Virology 189:10–20.

Hewat, E.A., Booth, T.F., Roy, P. (1994). Structure of correctly self–assembled bluetongue virus–like particles. Journal of Structural Biology 112:183–191.

Hewat, E.A., Booth, T.F., and Roy, P. (1992). Structure of bluetongue virus particles by cryoelectron microscopy. Journal of Structural Biology 109:61–69.

Hill–Perkins, M.S. and Possee, R. D. (1990). A baculovirus expression vector derived from the basic protein promoter of *Autographa californica* nuclear polyhedronis virus. Journal of General Virology 71:971–976.

Hyatt, A.D., Zhao, Y. and Roy, P. (1993). Release of bluetongue virus–like particles from insect cells is mediated by BTV nonstructural protein NS3/NS3A. Virology 193:592–603.

Kitts, P.A. and Possee, R.D. (1993). A method for producing recombinant baculovirus expression vectors at high frequency. BioTechniques 14(5):810–817.

LeBlois, H., Fayard, B., Urakawa, T., and Roy, P. (1991). Synthesis and characterization of chimeric particles between eipzootic hemorrhagic disease virus and bluetongue virus: functional domains are conserved on the VP3 protein. Journal of Virology, 65(9):4821–4831.

Loudon, P.T., Hirasawa, T., Oldfield, S., Murphy, M. and Roy, P. (1991). Expression of the outer capsid protein VP5 of two bluetongue viruses, and synthesis of chimeric double–shelled virus–like particles using combinations of recombinant baculoviruses. Virology 182:793–801.

Loudon, P.T., and Roy, P. (1991). Assembly of five bluetongue virus proteins expressed by recombinant baculoviruses: inclusion of the largest protein VP1 in the core and virus–like particles. Virology 180:798–802.

Loudon, P.T., and Roy, P. (1992). Interaction of nucleic acids with core–like and subcore–like particles of bluetongue virus. Virology 191:231–236.

Martinez–Torrecuadrada, J.L., Iwata, H., Venteo, A., Casal, I. and Roy, P. (1994). Expression and characterization of the two outer capsid proteins of African horsesickness virus: the role of VP2 in virus neutralization. Virology 202:348–359.

Merryweather, A.T., Weyer, U., Harris, M.P.G., Hirst, M., Booth, T., and Possee, R. D. (1990). Construction of genetically engineered baculovirus insecticides of the *Bacillus thuringiensis* subsp. *kurstak* HD–73 delta endotoxin. Journal of General Virology 71:1535–1544.

Roy, P., Bishop, D.H.L., LeBlois, H., and Eramus, B.J. (1994). Long–lasting protection of sheep against bluetongue challenge after vaccination with virus–like particles: evidence for homologous and partial heterologous protection. Vaccine 12(9):805–812.

Roy, P., French, T., and Erasmus, B.J. (1992). Protective efficacy of virus–like particles of bluetongue disease. Vaccine 10(1):28–32.

Stewart, L.M.D., Hirst, M., Ferber, M.L. Merryweather, A.T., Cayley, P.J., and Possee, R.D. (1991). Construction of an improved baculovirus insecticide containing an insect–specific toxin gene. Nature 352: Letters to Nature.

Takehara, K., Ireland, D., and Bishop, D.H.L. (1988). Co–expression of the Hepatitis B surface and core antigens using baculovirus multiple expression vectors. Journal of General Virology 69:2763–2777.

Weyer, U., Knight, S., and Possee, R.D. (1990). Analysis of very late gene expression of *Autographa californica* nuclear polyhedrosis virus and the further development of multiple expression vectors. Journal of General Virology 71:1525–1534.

Weyer, U. and Possee, R.D. (1991). A baculovirus dual expression vector derived from the *Autographa calinica* nuclear polyhedrosis virus polyhedrin and p10 promoters: co–expression of two influenza virus genes in insect cells. Journal of General Virology 72:2967–2974.

Ahn, B.Y., Rosel, J., Cole, W.B., and Moss, B.: Identification and expression of rpo19, a vaccinia virus gene encoding a 19–kilodalton DNA–dependent RNA polymerase subunit. J. Virol. 66:971–982 (1992).

Cussac, V., Ferrero, R.L. and Labigne, A.: Expression of Helicobacter pylori urease genes in *Escherichia coli* grown under nitrogen–limiting conditions. J. Bacteriol. 174:2466–2473 (1992).

Janeway, C. A., Jr.: The T cell receptor as a multicomponent signalling machine. Annu. Rev. Immunol. 10:645–674 (1992).

Malpartida, F. and Hopwood, D.A.: Molecular cloning of the whole biosynthetic pathway of a Streptomyces antibiotic and its expression in a heterologous host. Nature 309:462–464 (1984).

Oldfield, S., Adachi, A., Urakawa, T., Hirasawa, T., and Roy, P.: Purification and characterization of the major group–specific core antigen VP7 of bluetongue virus synthesized by recombinant baculovirus. Journal of General Virology 71:2649–2656 (1990).

Possee, R. D.: Cell surface expression of influenza virus haemagglutinin in insect cells using a baculovirus vector. Virus Res. 5:43–59. (1986).

Possee, R.D. and Howard, S.C.: Analysis of the polyhedrin gene promoter of the *Autographa californica* nuclear polyhedrosis virus. Nucleic Acids Res. 15:10233–10248 (1987).

Roy, et al.: Structure of the Bluetongue Virus Genome And Its Encoded Proteins. In Roy, P. & Gorman,B.M. (eds.), Bluetongue Viruses–Current Topics in Microbiology and Immunology. Springer–Verlag, Heidelberg pp. 43–80.

Roy, P., Adachi, A., Urakawa, T., Booth, T. F. and Thomas, C.P.: Identification of bluetongue virus VP6 protein as a nucleic acid–binding protein and the localization of VP6 in virus–infected vertebrae cells. Journal of Virology 64:1–8 (1990).

Thomas, C.P. Booth, T.F. and Roy, P.: Synthesis of bluetongue virus–encoded phosphoprotein and formation of inclusion bodies by recombinant baculovirus in insect cells: it binds the single–stranded RNA species. Journal of General Virology 71:2073–2083 (1990).

Urakawa, T., and Roy, P.: Bluetongue virus tubules made in insect cells by recombinant baculoviruses: expression of the NS1 gene of bluetongue virus serotype 10. Journal of Virology 62:3919–3927 (1988).

Woychik, W.A. and Young, R.A.: RNA polymerase II: subunit structure and function. Trends Biochem. Sci. 15:347–351 1990).

Ono, et al: The complete nucleotide sequences of the cloned hepatitis B virus DNA; subtype adr and adw Nucleic Acids Research 11(6):1747–1757 (1983).

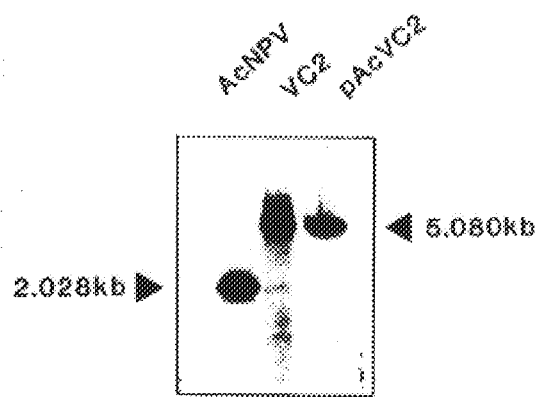
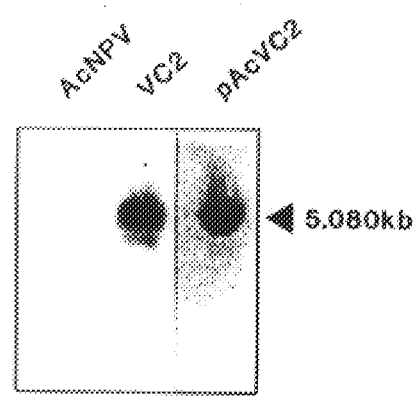
FIG.3a  FIG.3b
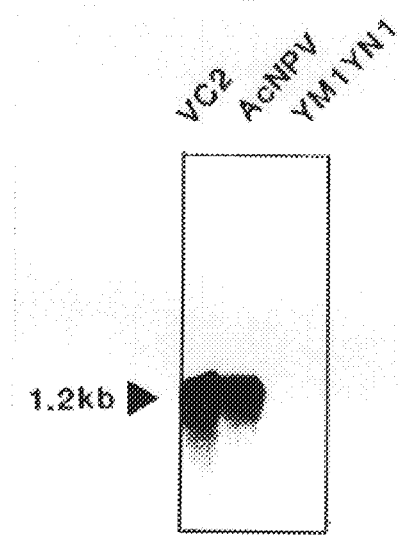
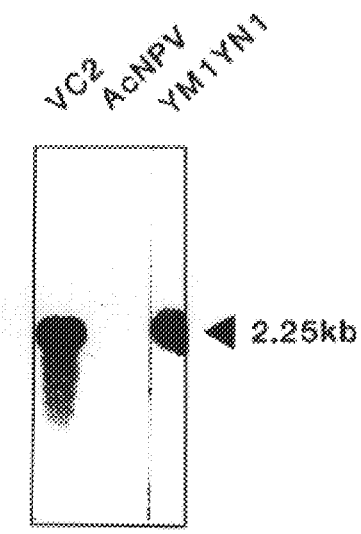
FIG.4a  FIG.4b

...AAATACGGATCCGAGGACTGGGGACCCTGTGACGAACATGGAG...

Construction of an expression vector to produce HBsAg

Construction of multiple expression vectors to produce HBsAg and HBcAg.

Construction of a multiple expression vector to produce HBsAg and Polyhedrin

HBcAg

HBsAg

EXPRESSION VECTORS FOR THE SYNTHESIS OF PROTEINS AND PLASMID REPLICONS AND SEQUENCE CASSETTES FOR USE IN CONSTRUCTING SUCH VECTORS

This application is a continuation-in-part of U.S. patent application Ser. No. 08/423,302 filed on Apr. 18, 1995, now abandoned which in turn is a continuation of U.S. Ser. No. 08/245,512, filed on May 11, 1994, now abandoned which in turn is a continuation of U.S. Ser. No. 08/102,549, filed on Aug. 5, 1993, now abandoned which in turn is a continuation of U.S. Ser. No. 07/940,759, filed on Sep. 8, 1992, now abandoned which in turn is a continuation of U.S. Ser. No. 07/346,942, filed on May 5, 1989, now abandoned which in turn is a continuation of International filing PCT Serial No. PCT/GB88/00663, filed on Aug. 11, 1988.

This invention relates to expression vectors for the expression of proteins, particularly eukaryotic proteins, and to plasmid replicons and sequence cassettes useful in constructing such vectors. The invention particularly relates to improved expression vectors useful for expressing selected proteins in insects and insect cells.

To address some of the more challenging aspects of molecular biology, for example, the synthesis of products involving multiple proteins, the investigation of the factors involved in heterologous protein-protein interactions and the synthesis of products involving consecutive enzymatic processes, new expression systems that produce several gene products simultaneously are required (so-called "polygenic expression"), including ones that can reproducibly make different proteins at different predetermined levels.

This particularly applies to hepatitis B surface and core antigens. That is to say it would be particularly desirable in order to produce diagnostic reagents and vaccines to be able to co-produce Hepatitis B surface and core antigens. Hepatitis B is a disease of major significance world-wide. Infected individuals may experience only an acute infection, or may develop a long term infection that is associated with liver cirrhosis and hepatocellular carcinoma, chronic active HB, chronic persistent HB and chronic lobular HB. In certain regions of the world, particularly, but not exclusively in South-east Asia and Africa, persistent infections may account for up to 15% of the population with as many as 40% of those individuals liable to die from one or another form of the disease. Estimates have been made that worldwide up to 300 million people are carriers of the disease (i.e., persistently infected with the virus). Plasma and rDNA derived preparations that contain the HbsAg have been used to vaccinate people against the disease.

A difficulty which often arises when attempting to produce new constructs which combine in a single expression vector genes coding for different proteins is that it can be difficult to select recombinant entities containing both desired genes in functional form or in a form in which the gene products can be expressed in predetermined quantities. Further the constructs obtained can be genetically unstable, that is to say naturally occurring recombinational events can result in loss of one or more of the introduced genes from the vectors or from the plasmid replicons used to produce them.

The production of eukaryotic proteins using expression vectors derived from the *Autographia californica* nuclear polyhedrosis virus has been described, e.g. by Smith et al., "Modification and Secretion of Human Interleukin-2 Produced in Insect Cells by a Baculovirus Expression Vector", Proc. Natl. Acad. Sci. USA, 82 No. 24 (1985) 8404–8408 and by Matsuura et al., "Baculovirus Expression Vectors: The Requirement for High Level Expression of Proteins, Including Glycoproteins", J. Gen. Virol. (1987) 68, 1233–1250. However in available baculovirus expression systems, no ready means exists which enables the expression of more than one gene product simultaneously in a reproducible manner. Further, available expression vectors lack the infective capability of the native virus. This is believed to be due to the fact that native virus produces, during late stages of infection, so-called inclusion bodies formed from a protein, polyhedrin, which is encoded in the native viral genome. Recombinant expression vectors designed to express desired proteins in the baculovirus expression system hitherto have sought to produce the desired protein in favour of polyhedrin. The expression vectors cannot readily be produced in the form of inclusion bodies—a form which is known to be particularly infective of insect larvae.

Chakrabarti et al. in an article entitled "New Vaccinia Virus Expression Vector" (Vaccines 86, Publn Cold Spring Harbour Laboratory and Chem. Abst. 105 (1986) 166241r) described a coexpression vector in the vaccinia system that coexpresses the β-Gal gene of *E. coli* and a second foreign gene. Expression of the β-Gal gene is used to screen for recombinant vaccinia virus. However no procedures are described enabling the reproducible expression of a plurality of eukaryotic proteins.

The present invention provides plasmid replicons, sequence cassettes and expression vectors in which the deficiencies of the prior art are avoided or substantially diminished.

Particularly multiple expression vectors that make foreign gene products as well as polyhedrin protein have now been developed. Since such recombinant viruses are occluded they are highly infectious in caterpillar hosts that are permissive for the parent virus, allowing the production of the foreign gene product in a cost effective manner. Multiple expression vectors have also been developed in which two foreign gene products are made by a recombinant virus (e.g., HBcAg and HBsAg), as well as occluded recombinant viruses that make HBsAg, and single expression vectors that make high levels of HBcAg, or HBpcAg.

According to one aspect of the present invention there are provided plasmid replicons for use in introducing a plurality of genes into an expression vector, comprising double-stranded DNA having (a) one or more sequences allowing the replicon to be reproduced in a bacterial host, (b) first and second sequences which are adapted to permit an intervening sequence located between said first and second sequences to be introduced into an expression vector, and (c) an intervening sequence located between said first and second sequences.

The plasmid replicons are characterised in that the intervening sequence comprises first and second polypeptide expression sequences (PESs) wherein each PES includes (i) a transcriptional promotor (ii) a unique restriction site for introduction of a gene which is native or foreign to the expression vector and (iii) a transcriptional termination site. Preferably each PES includes a different unique restriction site for introduction of a gene which is native or foreign to the expression vector.

The term "PES" will be used hereafter to denote "polypeptide expression sequence".

In order to reduce the possibility of recombinational elimination of desired introduced genes, the first and second PESs are advantageously arranged in the opposite sense to one another on separate strands of the DNA.

Alternatively the first and second PESs may be arranged in the same sense on the same strand of DNA. With this construction it is particularly preferred that a selectable gene or an essential functional gene for the expression vector is located between the two PESs to select against derivatives that have eliminated one or other PES by, e.g. natural recombination.

In order to prepare the plasmid replicons for introducing a plurality of genes into an expression vector capable of transfecting a susceptible insect or insect cell, genes which are native or foreign to the expression vector may be introduced at the sites (ii) of the PESs. The resulting "loaded" plasmid replicons, i.e. plasmid replicons loaded with desired genes for introduction into an expression vector form a further aspect of the present invention. Such "loaded" plasmid replicons comprise double stranded DNA having (a) one or more sequences allowing the replicon to be reproduced in a bacterial host, (b) first and second sequences which are adapted to permit an intervening sequence located between said first and second sequences to be introduced into an expression vector, and (c) an intervening sequence located between said first and second sequences, and are characterised in that the intervening sequence comprises first and second polypeptide expression sequences (PESs) wherein each PES includes (i) a transcriptional promotor (ii) a gene which is native or foreign to the expression vector and (iii) a transcriptional termination site. The transcriptional termination site can be native or foreign to the expression vector.

Advantageously, the plasmid replicons according to the invention are used to constuct vectors capable of transfecting susceptible insect cells. Examples include vectors derived from viruses, the wild type or derivatives of which are capable of infecting such cells. In such cases one or more of the genes present in the PESs may code for viral protein normally expressed during infection of the cells by wild type virus.

Alternatively or additionally the gene introduced into at least one the PESs may represent a selectable foreign protein or a normal gene product of the vector.

The production of one or more selectable or normal gene products may then be used as marker(s) for the detection of desired recombinant plasmid replicons or expression vectors. Further, at least one of said promoters in the PESs may be a promotor for a viral protein normally expressed during infection of the cells by wild type virus.

The plasmid replicons according to the invention (both loaded and unloaded) may be constucted from so-called "sequence cassettes" which themselves form a further aspect of the invention. These sequence cassettes comprise recombinant DNA molecules having an intervening sequence which comprises first and second polypeptide expression sequences (PESs) wherein each PES is as defined above either for the loaded or unloaded plasmid replicons, flanked by arms which are homologous with sequences of an expression vector, such that when inserted in the vector, no essential functional genes of the expression vector are lost.

In a first preferred constuction of sequence cassette, the arms are homologous to sequences of the vector genome, which sequences are arranged so as to allow the intervening sequences to be introduced without loss of vector DNA sequences.

In a second preferred construction the arms are homologous to sequences of the vector genome, which sequences are arranged so as to allow the intervening sequences to be introduced with replacement of inessential vector DNA sequences by intervening sequences of the sequence cassette.

In a third preferred construction the arms are homologous to sequences of the vector genome, which sequences are arranged so as to allow the intervening sequences to be introduced so as to replace intergenic or non-regulatory regions of the vector genome.

Sequence cassettes, according to the invention may be constructed in sets wherein the homologous regions of each cassette of the set are homologous to different regions of the vector genome, allowing a plurality of pairs of PESs to be introduced into the vector genome, with each pair being located at a separate location.

Expression vectors, suitable for transfecting insect cells may be produced from the plasmid replicons defined above. These expression vectors are themselves novel and form a further aspect of the invention and have an insert adapted to direct synthesis in the cell of at least one polypeptide not normally encoded by nuclear DNA of the cell, said insert comprising double-stranded DNA having an intervening sequence located between said first and second sequences. The expression vectors are characterised in that the intervening sequence comprises first and second polypeptide expression sequences (PESs) wherein each PES includes (i) a transcriptional promotor (ii) a gene which is native or foreign to the expression vector and (iii) a transcriptional termination site. The transcriptional termination site can be native or foreign to the expression vector.

These expression vectors may be derived from a viral entity, the wild type of which is infectious of insect cells. In this case one of said structural genes may advantageously code for a viral protein normally expressed during infection of the cells by wild type virus. In these preferred expression vectors at least one of said promoters can be a promotor for a viral protein normally expressed during infection of the cells by wild type virus.

Specific examples of expression vectors according to the invention derived from viruses are ones wherein the viral entity is a baculovirus. In this case one of said structural genes codes can conveniently code for AcNPV polyhedrin protein and at least one of said promoters can be the promotor of the polyhedrin gene of *Autographa calfornica* nuclear polyhedrosis virus.

Recombinant plasmid replicons and expression vectors according to the invention may comprise only a single pair of said PESs or they may include a plurality of such pairs. Thus they may be derived from only a single cassette of the kind described above or they may be derived from a plurality of such cassettes.

In the latter case it is preferable that there are one or more essential functional genes or selectable genes located between the PESs with regulatory elements and sequences of these essential or selectable genes being distinguished from those of the PESs. By constructing plasmid replicons and expression vectors in this way it is possible to reduce or minimise the likelihood of gene elimination by recombination.

The plasmid replicons referred to herein generally can be plasmids which can replicate in a bacterial host with or without introduced genes. Any introduced genes can include ones that may be expressed in the bacterial host, e.g. β-galactosidase under control of a bacterial plasmid promoter to allow selection of recombinant plasmids in bacteria, genes which may be expressed only in a eukaryotic host, e.g. β-galactosidase under control of a eukaryotic (e.g. viral) promoter to allow selection of recombinant viruses in a eukaryotic host, or genes coding for eukaryotic proteins.

One particular example of a plasmid replicon/expression vector system according to the invention is the system based on the polyhedrin gene promoter of the insect *Autographa californica* nuclear polyhedrosis virus (AcNPV), a baculovirus which has been increasingly utilized as an expression vector to synthesize a wide variety of eukaryotic gene products (Smith et al., 1983; Pennock et al., 1984; Miyamoto et al., 1985; Smith et al., 1985; Matsuura et al., 1986, 1987; Possee, 1986; Kuroda et al., 1986; Estes et al., 1987; Inumaru and Roy, 1987, Overton et al., 1987). The basis for expression in this system is the use of the AcNPV polyhedrin promotor, a major late promotor that in wild-type AcNPV infections leads to the production of polyhedrin protein which assembles to form visible polyhedral inclusion bodies that occlude virions in the nucleus of the infected cell.

Replacement of the polyhedrin gene sequence in a suitable plasmid replicon with a foreign gene, followed by transfection of *Spodoptera frugiperda* cells with the derived plasmid in the presence of infectious AcNPV DNA, results in the production of recombinant expression vectors (viruses) that express the foreign gene product in lieu of the polyhedrin protein (Smith et al., 1983). Such recombinants can be selected by virtue of their polyhedrin-negative phenotype or other properties, for examples those ascribable to the presence of the foreign gene.

Although the level of expression of the foreign gene product has been found to be variable, recent work has established that the level of expression of a foreign protein in this system is directly related to elements of the DNA sequence between the transcription initiation and the translation initiation site of the polyhedrin gene and that high levels of expression are obtainable when all those sequence elements are present (Matsuura et al., 1987). These studies have resulted in the construction of a new plasmid replicon, pAcYM1, which has been utilized to produce recombinant viruses that express to high levels the gene products of the ambisense S RNA of lymphocytic choriomeningitis (LCMV) virus (Romanowski et al., 1985; viz: either the LCMV nucleocapsid protein, N, or the LCMV glycoprotein precursor, GPC). The levels of synthesis of these proteins by the respective recombinant viruses approach those of the polyhedrin protein made in wild-type AcNPV infections (i.e., ca. 25–50% of the total cell or insect protein).

Examples of multiple expression vectors according to the invention have been constructed using AcNPV baculovirus expression systems. Using these systems, we have duplicated the AcNPV polyhedrin promoter and its associated transcription termination signals to yield a plasmid replicon, pAcVC2, that contains both the AcNPV polyhedrin gene and the LCMV-N protein each under the control of separately organized polyhedrin promoters. Since. both gene products are known to be produced to a high level when expressed individually (Matsuura et al., 1987), the isolation of recombinant viruses using the pAcVC2 plasmid allowed us to assess the ability of the baculovirus system to produce two different gene products simultaneously using the duplicated polyhedrin promoter arrangement. Once the viability of this approach was established, general purpose AcNPV-based plasmid replicons were produced containing a cassette of two PESs with insertion sites for two genes. To minimise recombinational elimination the two PESs were arranged in non-overlapping sequences in opposite orientation (viz: separate DNA strands). However the invention does not exclude the posibility of organization in series (viz: on the same strand with or without intervening sequences).

General purpose plasmid replicons of the kind described can be used to insert pairs of genes into a viral expression vector. Such pairs or additional pairs of genes can be inserted into the viral genome at multiple sites for polygenic expression by incorporating the corresponding cassettes into intergenic regions (or into non-essential genes) in plasmid replicons containing other parts of the AcNPV genome.

In more detail and by way of example, a copy of the polyhedrin gene promoter of *Autographa californica* nuclear polyhedrosis virus (AcNPV) in association with the coding region of lymphocytic choriomeningitis virus N protein (LCMV-N) and the relevant polyhedrin transcription termination signals, was cloned into the unique EcoRV site of a plasmid representing an Eco RI derived fragment of the AcNPV genome. The cloning site was upstream of the natural AcNPV polyhedrin gene of the desired recombinant plasmids and the one with the LCMV-N and polyhedrin genes in opposite orientation to each other was selected, to minimise gene elimination by natural recombinational events.

The derived recombinant pAcVC2 plasmid had, therefore, both the normal polyhedrin gene and the LCMV-N gene each with its own copy of the polyhedrin transcriptional machinery.

Co-transfection of *Spodoptera frugiperda* insect cells with the pAcVC2 plasmid together with infectious polyhedrin-negative AcNPV DNA, resulted in the isolation of recombinant viruses that made polyhedrin protein as well as LCMV-N protein. Electron microscopy demonstrated the presence of occluded virus particles in the nucleus of the recombinant virus infected cells and aggregates of LCMV-N protein in the cytoplasm of the same cells. Unlike polyhedra-negative AcNPV recombinants, the occluded recombinants were potent infectious agents for the caterpillar *Trichoplusia ni*.

In a similar manner DNA sequences coding for hepatitis B surface and core antigens have been cloned into unique EcoRV and AccII sites of an EcoRI derived fragment of the AcNPV genome. Recombinant plasmids were produced containing (i) the polyhedrin gene and the hepatitis B surface antigen gene and (ii) the hepatitis B surface antigen gene and the hepatitis B core antigen gene.

Co-transfection of *Spodoptera frugiperda* insect cells with these plasmids together with infectious polyhedrin-negative AcNPV DNA, resulted in the isolation of recombinant viruses that made (i) polyhedrin protein as well as hepatitis B surface antigen and (ii) hepatitis B surface antigen and hepatitis B core antigen.

EXAMPLES

The construction of multiple expression vectors according to the invention will be described in more detail in the following Examples.

Example 1

(i) PROCEDURES

A. Construction of the plasmid replicon pAcVC2 containing LCMV-N and AcNPV polyhedrin genes The method chosen to make a baculovirus plasmid replicon that would ultimately contain two gene products under the control of the necessary regulatory sequences required the duplication of the polyhedrin promoter and transcription termination sequences. The transcriptional initiation and terminator sites for the polyhedrin mRNA species have been mapped to, respectively, approximately 48 nucleotides upstream of the translation initiation codon and 376 nucleotides downstream of the translation termination codon (Howard et al., 1986). Since transcription termination occurs downstream of the sequence motif AATAAA, a sequence corresponding to the normal eukaryotic polyadenylation signal (Birnstiel et al., 1985), it has been suggested that baculovirus mRNAs may be cleaved and polyadenylated by the 3'mRNA processing machinery of the host (see Rohrmann, 1986). By contrast, the precise sequence elements required for the promoter activity of the polyhedrin gene have not been ascertained, although DNA sequence elements commonly observed in association with RNA polymerase II driven transcription can be identified in the sequences that are upstream of the translation initiation site. Therefore, we envisaged that in order to duplicate the required information for the mRNA synthesis and regulation of a foreign gene under the control of the polyhedrin transcriptional machinery a restriction fragment was required that contained DNA sequences some distance upstream of the known transcription initiation site and downstream of the sequences encompassing the replicon termination site. To this end, an available plasmid replicon containing the LCMV-N gene (pAcYM1.YN1, Matsuura et al., 1987) which could yield recombinant viruses that made high levels of LCMV-N protein was used as substrate. It was treated with the restriction endonuclease AccII and the 3052 nucleotide fragment, containing the relevant polyhedrin transcriptional initiation and termination machinery in association with the LCMV-N-gene (FIG. 1), was isolated by standard procedures (Maniatis et al., 1982). Having recovered DNA which should encompass the polyhedrin gene promoter and terminator sequences a plasmid containing the authentic polyhedrin gene was required. The EcoRI "I" fragment in pUC8 was selected (Possee, 1986). Initially, the 3052 base pair fragment was placed within the 3' non-translated region of the polyhedrin gene and in the same orientation as the polyhedrin coding sequence since this region of the AcNPV genome had been utilized previously in our laboratory to insert a synthetic oligonucleotide for the environmental release of a genetically marked baculovirus (Bishop, 1986). However, plasmids containing the AccII fragment in this position did not yield recombinant viruses. Although the reason this did not work is not known, the likely cause was deletion of the inserted gene by homologous sequence recombination. Therefore as an alternative approach, we selected an insertion site in the 5' upstream region of the polyhedrin gene. Notwithstanding the paucity of biochemical data regarding the sequence elements essential for high level polyhedrin gene promoter activity, the unique EcoRV restriction endonuclease site that is located in a non-coding region some 100 nucleotides upstream of the polyhedrin ATG in the AcNPV EcoRI "I" fragment was chosen for insertion of the 3052 nucleotide AccII fragment containing the LCMV-N gene. Since the insertion involved a blunt end ligation, the AccII and EcoRV sites were destroyed by this procedure. Following ligation and transformation, recombinant plasmids were obtained and analysed by restriction endonuclease digestion. Clones were selected that contained the duplicated promoter and coding region for the LCMV-N gene in the oppsite orientation to that of the resident polyhedrin gene (see FIG. 1). Such a configuration should restrict the possibility of homologous sequence genetic recombination and the excision of one or other of the genes of interest from progeny viruses. A derived plasmid replicon, designated pAcVC2, was characterised and shown to have the LCMV-N and polyhedrin genes with their associated polyhedrin transcriptional machinery in the form shown in FIG. 1.

B. Preparation of a recombinant baculovirus containing the LCMV-N and the AcNPV polyhedrin genes The plasmid replicon pAcVC2 was co-transfected into Spodoptera frugiperda cells in the presence of an available recombinant, polyhedrin-negative, helper viral DNA. After transfection, putative recombinant viruses (e.g., VC2) were isolated from the infected cells by selecting for progeny virus plaques that exhibited a polyhedrin-positive phenotype (ca. 0.1–1% frequency). The helper viral DNA (YM1.BTV-10.2) contained a nucleotide insert representing the major neutralization antigen VP2 of bluetongue virus serotype 10, RNA segment 2 (gift of P. Roy; see Inumaru and Roy, 1987) that had been previously manipulated into the polyhedrin-negative virus using the vector pAcYM1. This helper viral DNA was chosen for two reasons. First, the virus was polyhedrin-negative so that new recombinants could be easily selected from co-transfections involving YM1.BTV-10.2 viral DNA and plasmid replicons containing the polyhedrin gene on the basis of their reacquisition of a polyhedrin-positive phenotype. Secondly, unlike the pAcRP based plasmids, or those derived by Smith and Summers (1983), the helper contained no polyhedrin protein coding sequences (see Matsuura et al., 1987) thereby eliminating the possibility of recombination within the polyhedrin coding region. After three successive cycles of plaque purification stocks of VC2 virus were obtained and used for a range of biochemical analyses.

C. Immunofluorescence analysis of recombinant virus infected cells

S. frugiperda cells were infected with the pAcVC2 derived recombinant VC2 virus and prepared for immunofluorescence analysis using an LCMV-N monoclonal antibody (gift of M. J. Buchmeier, see Buchmeier et al., 1981). As controls, cells infected with either YM1.YN1 virus (containing only the LCMV-N coding region), or wild-type AcNPV were employed. The results, shown in FIG. 2, provided evidence for the expression of the LCMV-N protein in the VC2 infected cells (FIG. 2e) that was comparable to that observed for the recombinant baculovirus expressing only the LCMV-N protein (YM1.YN1, FIG. 2c). As expected, cells infected with wild-type AcNPV did not exhibit positive immunofluorescence (FIG. 2a).

In addition to ultraviolet microscopy, examination of virus infected cells using a light microscope revealed the presence of polyhedral inclusion bodies in control wild-type AcNPV infected cells (FIG. 2b) and in cells infected with the VC2 recombinant virus (FIG. 2g). All the cells infected with the VC2 virus exhibited both LCMV-N immunofluorescence and polyhedral inclusion bodies (compare FIG. 2e and 2g). This phenomenon is most clearly seen in the hybrid ultraviolet/visible light micrograph presented in FIG. 2f. As shown previously (Matsuura et al., 1987) cells infected with the recombinant virus containing the LCMV-N gene in lieu of the polyhedrin gene (i.e., virus YM1.YN1) did not exhibit polyhedral inclusion bodies although they had a marked granular appearance (FIG. 2d). In summary, the data clearly demonstrated that cells infected with the VC2 virus expressed LCMV-N protein and polyhedrin simultaneously.

D. Location of the genes for LCMV-N protein and AcNPV polyhedrin protein within the recombinant VC2 viral DNA Although the immunofluorescence data shown in FIG. 2 indicated that the genes for LCMV-N and polyhedrin were expressed in cells infected with the VC2 virus, it was essential to demonstrate that during the co-transfection re-ime the genes had been incorporated into the viral genome in the desired orientation (as in pAcVC2, see FIG. 1) rather than at random. Conveniently, digestion of the recombinant plasmid pAcVC2 with the restriction endonuclease AccII yields a 5080 nucleotide fragment that contains both the LCMV-N gene and the polyhedrin gene. This enzyme was therefore used for Southern analysis of the recombinant VC2 virus. DNA preparations obtained from pAcVC2 plasmids or from purified VC2, or AcNPV, virions were digested with AccII and resolved by agarose gel electrophoresis. Southern blot analyses of these preparations using radioactive probes specific for the coding region of either the AcNPV polyhedrin or the LCMV-N (Matsuura et al., 1987) gene are shown in FIG. 3. The data demonstrated that both the polyhedrin and LCMV-N gene specific probes hybridized to a 5082 nucleotide fragment in the AccII digested VC2 viral DNA that correlated to the AccII fragment detected with both probes in the plasmid replicon pAcVC2. As expected, the polyhedrin probe hybridized to a 2028 nucleotide AccII fragment encompassing the polyhedrin gene in wild-type AcNPV DNA, whilst the LCMV-N probe did not hybridize to any of the AcNPV DNA sequences. The results indicated that both the LCMV and polyhedrin coding sequences were incorporated into the desired area of the VC2 viral genome.

E. Expression of LCMV-N and polyhedrin gene products by the VC2 virus

The presence of LCMV-N and polyhedrin mRNA species in cells infected with the recombinant VC2 virus was determined by Northern analysis. As controls, *S.frugiperda* cells were infected with AcNPV and the YM1.YN1 recombinant virus (Matsuura et al. , 1987). Infected cell nucleic acids were extracted at 24 h post-infection and chromatographed on columns of oligo(dT) cellulose to select RNA with polyadenylic acid sequences. The poly(A+) and poly (A−) RNA preparations were treated with methylmercuric hydroxide and separated into size classes by agarose gel electrophoresis also in the presence of methylmercuric hydroxide. RNA was blotted and fixed to Hybond-N, then probed with nick-translated DNA representing either the LCMV-N or the AcNPV polyhedrin gene. The results of such analyses are shown in FIG. 4. The polyhedrin probe hybridized to a 1.2 kb mRNA species in both the VC2 and AcNPV infected cells but did not hybridize to any mRNA species produced in the YM1.YN1 recombinant virus infection. In contrast, the LCMV-N probe hybridized to an mRNA species ca. 2.25 kb in length in both the VC2 and YM1.YN1 virus infected cells. The size of this mRNA species corresponds to the predicted length of the LCMV-N mRNA if the authentic polyhedrin transcriptional machinery had been utilized. These mRNA size analyses confirmed and provided independent evidence that the LCMV-N and polyhedrin genes were under separate transcriptional control. As expected neither polyhedrin, nor LCMV-N, mRNA species were present in the poly(A−) RNA tracts (data not shown). As far as could be ascertained by such analyses, the data exhibited in FIG. 4 indicated that the levels of polyhedrin and LCMV-N mRNA in the VC2 virus infected cells were essentially comparable to those produced by cells infected with either AcNPV or YM1.YN1 virus.

In order to determine the relative amounts of LCMV-N protein and the polyhedrin protein synthesized in the VC2 virus infected *S. frugiperda* cells, cells were pulse-labelled at various times post-infection and the radio-labelled proteins analysed by polyacrylamide gel electrophoresis. The results of pulse-labelling VC2 virus-infected cells with [$^{35}$S] methionine at 24 h and 48 h post-infection are shown in FIG. 5*a*. It was apparent that in the VC2 virus infected cells there were two major [$^{35}$S]-labelled protein products with sizes corresponding to $62\times10_3$ Da and $33\times10^3$ Da. By comparison with the [$^{35}$S]-labelled proteins synthesized in insect cells infected with the polyhedrin-negative YM1.YN1 virus, or with the AcNPV virus, the VC2 directed protein products corresponded, respectively, to the LCMV-N protein ($62\times10^3$ Da) and the AcNPV polyhedrin protein ($33\times10^3$ Da). The relative level of LCMV-N and polyhedrin gene expression apparent in the pulse-labelled protein analyses was confirmed by analyses of stained protein gels (FIG. 6*b*). This result also provided evidence that both proteins accumulated to substantial levels in the VC2 virus infected cells.

As discussed above, the LCMV-N gene in the recombinant VC2 virus was located in a position that was upstream, but in the opposite orientation, relative to the normally positioned polyhedrin gene. It is of interest to note, therefore, that the level of LCMV-N expression by the VC2 virus did not differ significantly from that observed with the recombinant baculovirus YM1.YN1 that expresses only LCMV-N (FIGS. 5 and 6). The level of polyhedrin protein expression in the recombinant VC2 virus infected cells was comparible in molar terms with that obtained for the LCMV-N protein (FIGS. 5 and 6).

F. Electron microscopic analyses of VC2 virus infected cells

It has been previously noted (Matsuura et al., 1987) that electron micrographs of insect cells expressing large amounts of LCMV-N protein contained multiple inclusion bodies in the cytoplasm which, on the basis of the intense cytoplasmic fluorescence observed with LCMV-N monoclonal antibody, were ascribed to LCMV-N protein aggregates. A similar analysis of cells infected with the recombinant VC2 virus is shown in FIG. 7. By comparison with uninfected cells (FIG. 7*a*), AcNPV (FIG. 7*b*), or YM1.YN1 (FIG. 7*c*) infected cells, two features of the VC2 virus infections were apparent; firstly, as in the YM1.YN1 virus infected cells, LCMV-N protein was present in aggregated form in cytoplasmic inclusions and secondly, as in wild-type AcNPV infections, the nucleus contained polyhedral bodies (FIG. 7*d*) with occluded virus particles (FIG. 7*e*).

G. Expression of LCMV-N Protein and Polyhedrin in ïT.niôlarvae

Since electron micrographs of ïS. frugiperdaô cells infected with the VC2 virus had revealed the presence of VC2 virions occluded within polyhedra, the latter were recovered and used to infect third instar ïT.niô caterpillars. For comparison, cell released virus (titre $8\times10^7$ pfu/ml) obtained from the supernatant fluids of VC2 virus infected ïS. frugiperdaô cells was also used to infect third instar ïT.niô caterpillars. After four days post-infection and prior to death of the larvae, a random selection of 5 caterpillars from each infection group (40 caterpillars per group) were extracted and their proteins resolved by polyacrylamide gel electrophoresis. The results of the stained protein gel analyses of these caterpillar extracts are shown in FIG. 5. Of the five caterpillars that received cell released virus (average caterpillar weight: 97 mg), only caterpillar no. 3 exhibited an infection and the concomitant production of small quantities of LCMV-N protein. In contrast, caterpillars infected with the VC2 derived polyhedral inclusion bodies were significantly smaller in size (average weight: 33 mg) and all five caterpillars exhibited a virulent viral infection with the concomitant production of large quantities of both the LCMV-N and polyhedrin proteins. By comparison with known amounts of bovine serum albumin electrophoresed in parallel with the larval extracts, it was estimated that each larva contained at least 0.1 mg of LCMV-N protein.

(ii) MATERIALS AND METHODS USED IN THIS EXAMPLE (a) Viruses and cells

AcNPV and recombinant virus stocks were grown and assayed in confluent monolayers of ïSpodoptera frugiperdaô cells in medium containing 10%. foetal bovine serum according to the procedures described by Brown and Faulkner (1977).

(b) DNA manipulations and constructions of DNA clones Plasmid DNA manipulations were effected essentially as summarised by Maniatis and associates (1982). Restriction enzymes, T4 DNA ligase and the Klenow large fragment of DNA polymerase were purchased from Amersham, U.K., Calf intestinal alkaline phosphatase was obtained from Boehringer Mannheim Biochemicals (Mannheim, FRG).

(c) Construction of pAcVC2

The plasmid replicon pAcYM1.YN1 which contained the entire LCMV-N gene (Matsuura et al., 1987; Possee, 1986) was digested to completion with AccII and the 3052 nucleotide fragment containing the LCMV-N gene with its associated polyhedrin promoter and transcription termination sequences isolated by electrophoresis in 0.8% agarose. The AccII fragment was ligated into an EcoRV digested and dephosphorylated plasmid, pAcEcoRI "I", that contained a 7.3 kb AcNPV fragment in a modified pUC8 plasmid (Possee, 1986). After transformation and screening with nick-translated LCMV-N DNA, plasmids were obtained (FIG. 1, pAcVC2) that were characterised by restriction enzyme and sequences analysis (Chen and Seeburg, 1985). Those with the format of pAcVC2 shown in FIG. 1 were selected to produce the recombinant virus VC2.

(d) Transfection and selection of recombinant virus VC2 $S.$ $frugiperda$ cells were transfected with a mixture of plasmid pAcVC2 DNA and DNA representing a polyhedrin-negative virus derived from pAcYM1 containing the bluetongue virus serotype 10 segment 2 DNA (YM1.BTV-10.2, a gift from Professor P. Roy, University of Alabama in Birmingham, USA, see Inumaru and Roy, 1987) using a modification of the procedures described by Smith et al. (1983). YM1.BTV-10.2 DNA (1 $\mu$g) purified by the method of Smith and Summers (1978) was mixed with various concentrations of plasmid DNA (25–100 $\mu$g) and adjusted to 950 $\mu$l with Hepes buffered saline (20 mM Hepes, 1 mM $Na_2HPO_4$, 5 mM KCl, 140 mM NaCl, 10 mM glucose, pH 7.05). After precipitation with 50 $\mu$l of 2.5M $CaCl_2$ DNA was inoculated onto monolayers of $1\times10^6$ $S.$ $frugiperda$ cells in 35 mm tissue culture dishes and incubated for 1 hour at room temperature. The supernates were discarded and 1.5 ml of medium containing 10% foetal bovine serum was added. After 3 days incubation at 28° C., the supernates were harvested and titred in confluent monolayers of $S.$ $frugiperda$ cells. Plaques exhibiting occlusion bodies (viral polyhedra, as determined by transmission light microscopy) were recovered and retitred on $S.$ $frugiperda$ cells to obtain recombinant, polyhedrin positive virus. Following a third plaque purification, high titred stocks of recombinant virus were obtained (VC2, $10^7$ to $10^8$ pfu/ml).

(e) Extraction and characterisation of viral and cellular nucleic acids

Viral DNA and infected cell mRNA were prepared as described previously (Matsuura et al., 1986). For Southern analyses, viral DNA was digested to completion with AccII and the products resolved by electrophoresis in 0.8% Agarose (BRL, Madison, Wis.), then blotted to Hybond-N (Amersham, U.K.). After drying, the membranes were illuminated with ultraviolet light for 5 minutes and hybridized (Southern, 1975) to either nick-translated LCMV WE DNA obtained from clone Y-1-A (Matsuura et al., 1986), or to nick-translated AcNPV polyhedrin DNA (a gift from Dr. R. D. Possee, Institute of Virology, Oxford, U.K.). The membranes were washed and autoradiographed. Cellular mRNA preparations were treated with 10 mM methyl mercury hydroxide (Bailey and Davidson, 1976), resolved by electrophoresis in 1% agarose gels containing methyl mercury and transferred by blotting to Hybond-N. After blotting (Alwine et al., 1977), the membranes were dried and illuminated with ultraviolet light for 5 min, then hybridized to $^{32}$P-labelled nick-translation products of DNA representing the polyhedrin gene and LCMV-N gene as described by Denhardt (1966). Membranes were washed and autoradiographed.

(f) Protein analysis $S.$ $frugiperda$ cells were infected with virus at a multiplicity of 10 pfu/cell in 35 mm tissue culture dishes and labelled with 100 $\mu$Ci[$^{35}$S]-methionine (Amersham, 1131 Ci/mmol) for 1 h at the indicated time using methionine-free medium. Prior to labelling, the cells were incubated for 1 h in methionine-free medium to reduce the intracellular pools of the precursor. After the labelling periods, the media were removed, the monolayers rinsed three times with phosphate-buffered saline (PBS) and the cells lysed in 100 $\mu$l RIPA buffer (1% Triton X-100, 1% sodium deoxycholate, 0.5M NaCl, 0.05M Tris-HCl, 0.01M EDTA, 0.1% SDS, pH 7.4). Aliquots of the protein samples were boiled for 5 min in dissociation buffer (2.3% SDS, 10% glycerol, 5% $\beta$-mercaptoethanol, 62.5 mM Tris-HCl, 0.01% bromophenol blue, pH 6.8) and subjected to electrophoresis in discontinuous gels of 10% polyacrylamide as described by Laemmli (1970). After electrophoresis the gels were fixed in acetic acid (10% v/v) and impregnated with Amplify (Amersham, U.K.) and exposed at –70° C. to X-ray film. Alternatively, gels were stained with Kenacid Blue (Overton et al., 1987).

(g) Infection of $T.ni$ with recombinant VC2 virus

Third instar $T.ni$ caterpillars grown on semi-synthetic media (Hoffman et al., 1966) were infected per os with either cell-released, non-occluded, VC2 virus purified by differential centrifugation ($8\times10^4$ p.f.u./caterpillar), or VC2 polyhedral inclusion bodies (likewise purified, $4\times10^4$ polyhedral inclusion bodies per caterpillar). After 4 days of incubation the caterpillars were harvested. The caterpillars were weighed and individuals were selected at random and homogenised in PBS (200 $\mu$l) containing 0.02% sodium diethyldithiocarbamate. Aliauots (5 $\mu$l) from the homogenates were prepared for gel electrophoresis.

(h) Immunofluorescence analysis of recombinant virus infected cells $S.$ $frugiperda$ cells were infected with the VC2 recombinant virus and prepared for immunofluorescence analyses 36 h post-infection using an LCMV-N monoclonal antibody (Buchmeier et al., 1981). As controls, $S.$ $frugiperda$ cells infected with either YM1.YN1 virus (Matsuura, et al., 1987; containing only the LCMV-N coding region), or with wild-type AcNPV, were emoloyed. For immuno-flourescnt analyses, aliquots (5 $\mu$l) of $S.$ $frugiperda$ cells infected 36 h previously at a multiplicity of 10 pfu/cell were spotted onto glass slides and fixed with cold acetone for 10 min. The cells were washed in PBS and incubated for 1 h at 37° C. with 10 $\mu$l of a $\frac{1}{32}$ dilution of LCMV N-specific monoclonal antibody, kindly provided by Dr. M. Buchmeier (Scripps Clinic and Research Institute, La Jolla, Calif., U.S.A.). The slides were washed with PBS, the cells stained with fluorescein conjugated swine anti-mouse IgG antibody for 1 h at 37° C., washed again with PBS and examined for fluorescence.

(j) Construction of pAcVC3

Plasmid pAcYM1 was digested with the restriction enzyme BamHI and the 3' ends repaired with the Klenow fragment of DNA polymerase in the presence of all 4 deoxynucleoside triphosphates. The DNA was then dephosphorylated by treatment with alkaline phosphatase and ligated to a BglII linker (5' GAAGATCTTC 3'). Subsequent digestion with BglII followed by religation led to the recovery of a new vector, pAcYM2, containing a unique BglII site in lieu of the original BamHI site (FIG. 8).

To generate a plasmid in which two foreign genes could be inserted, each under the control of its own copy of the polyhedrin promoter, the 1.3 kb DNA fragment obtained by digestion of pAcYM2 with AccII was cloned into plasmid pAcYM1 that had been previously digested with EcoRV (FIG. 8). The ligation did not regenerate the AccII or EcoRV sites used in these digestions. Of the 2 possible orientations in which the fragment could be recovered in the new recombinant plasmid, the one with the polyhedrin transcription initiation sites next to each other but in opposite orientations was selected, pAcVC3 (FIG. 8). In this orientation the two putative transcription termination signals, AATAAA, were separated by the BglII and BamHI sites (FIG. 8). The construction of plasmid pAcVC3 allows one foreign gene to be inserted in the plasmid at the BamHI site and another into the BglII site. By this means each gene has its own, non-overlapping, copy of the polyhedrin transcription promoter and terminator sequences (i.e., representing two PESs). The orientation of the genes on different strands of the DNA, should minimize the possibility of gene excision by recombinational events.

(k) Preparation of recombinant virus VC4

Using the procedure described above for the production of virus VC2, but employing an available plasmid containing the gene coding for the Hantaan N protein (the protein corresponding to the Hantaan S (small) RNA—Schmaljohn, C. S.; Jennings, G. B.; Hay, J. and Dalrymple, J. M. "Coding stategy of the S-genome segment of Hantaan Virus"; Virology, 155, pp. 633–643 (1986)), recombinant virus VC4 was produced. This virus, when used to infect T.ni caterpillars enabled the concomitant production of polyhedrin protein and Hantaan N protein in those insects.

Using similar techniques, recombinant virus capable of expressing combinations of polyhedrin protein and Hepatitis B, S or C proteins may be produced.

Example 2

(i) PROCEDURES

A. Construction of Recombinant Transfer Vectors for Single Gene Expression

A 581 base-pair DNA fragment containing the coding region of the HB virus C gene and a 1005 base-pair fragment containing the coding region of the preC and C gene were excised with StyI and HinPI, respectively, from plasmid pSCK102 kindly supplied by C.-Y. Kang (University of Ottawa, Canada, representing an adw serotype of HB virus). Each fragment was repaired with the Klenow fragment of DNA polymerase, then cloned into the BamHI site of the baculovirus pAcYM1 vector (Matsuura et al., 1987). The derived recombinant transfer vectors were designated pAcMY1KTc and pAcY1KTpc respectively (FIG. 9). The entire S gene of HB virus was prepared by AccII digestion of plasmid pAcRP6-HBsYK14 (Kang et al., 1987), ligated into the BamHI site of pAcYM1, then digested with BamHI, and the resulting 725 base-pair DNA fragment containing the S gene inserted into the BamHI site of the pAcYM1 vector to construct the recombinant transfer vector pAcYM1KTs (FIG. 10).

B. Construction of Recombinant Transfer Vectors For Dual Gene Expression

Plasmid pAcYM1KTs was digested with AccII and the fragment containing the S gene, its associated polyhedrin promoter and transcription termination sequences was ligated into the dephosphorylated EcoRV digestion product of plasmid pAcYM1KTs to give the dual expression, recombinant transfer vector pAcVCKTsc, (FIG. 11), or into the EcoRV digestion product of pAcYM1KTpc to give the dual expression vector pAcVCKTspc, (FIG. 11). Insertion of the same HB S gene fragment into the 7.3 kb EcoRI 'I' fragment of AcNPV (in a modified pUC8 plasmid, Possee, 1986) yielded the recombinant transfer vector pAcVCKTs (FIG. 12).

C. Transfections and Selection of Recombinant Viruses

To obtain recombinant viruses that would express the foreign gene(s), S. frugiperda cells were transfected with mixtures of infectious AcNPV DNA and plasmid DNA representing the individual recombinant transfer vectors essentially as described by Overton and associates (1987). From cotransfection with pAcYM1KTc plasmid DNA recombinant virus YM1KTc was obtained, likewise from pAcYM1KTpc recombinant YM1KTpc, from pAcYM1KTs recombinant YM1KTs, from pAcVCKTspc recombinant VCKTspc, and from pAcVCKTsc recombinant VCKTsc. To derive an occluded recombinant virus that expressed both the HB S antigen and AcNPV polyhedrin protein, S. frugiperda cells were transfected with a mixture of plasmid pAcVCKTs DNA and DNA representing a polyhedrin negative virus derived from pAcSI.10.2 that contained the bluetongue virus serotype 10 segment DNA2 (Immumaru & Roy, 1987). Plaques of recombinant viruses (VCKTs) that contained visible occlusion bodies were recovered.

D. Extraction and Characterisation of Viral DNA

Viral DNA was prepared as described previously (Overton et al., 1987). DNA samples were digested to completion with AccII and the products subjected to Southern analyses as described by Matsuura and associates (1986).

E. Labelling and Analyses of Infected Cell Polypeptides

S. frugiperda cells were infected with virus at a multiplicity of 10 p.f.u./cell in 35 mm tissue culture dishes and incubated at 28° C. for 48 h. At the indicated times the cells were treated for 1 h with methionine-free medium, then labelled for 3 h with 15 $\mu$Ci of [$^{35}$S] methionine (Amersham International, 1131 Ci/mmol) in the same medium. On occasion, the cells were not labelled. The cells were rinsed three times with phosphate buffered saline (PBS) and lysed in 150 $\mu$l of RIPA buffer (1% Triton X-100, 1% sodium deoxycholate, 0.5M-NaCl, 0.5M-Tris-HCl, 0.01 M-EDTA, 0.1% SDS, pH 7.4). Portions of the protein samples were boiled for 5 min in dissociation buffer (2.3% SDS, 10% glycerol, 5% $\beta$-mercapto-ethanol, 62.5 mM-Tris-HCl, 0.01% bromophenol blue, pH 6.8) and subjected to electrophoresis (SDS-PAGE) in a discontinuous gel of 10–20% polyacrylamide containing SDS as described by Laemmli (1970). After electrophoresis the gel was fixed in acetic acid (10% v/v) and stained with Kenacid Blue, then exposed at –70° C. to X-ray film.

F. Immunoblotting Analysis

After SDS-PAGE, proteins were transferred electrophorectically to nitrocellulose membranes for 4 h at 150 mA. The membranes were soaked at 4° C. overnight in TBS (20 mM-Tris-HCl, pH7.4, 0.15M-NaCl containing 10% foetal calf serum). After another wash with TBS, the membranes were treated for 1 h at 20° C. with rabbit anti-HBcAg serum in TBS containing 5% foetal calf serum and 0.05% Tween 20 (TTBS). Following further washes with TTBS, bound antibodies were detected with goat antirabbit immunoglobulins conjugated to alkaline phosphatase (Sigma) and Fast Blue BB salt and $\beta$-naphthylphosphate (Sigma) as substrate.

G. Purification of HBcAg and HBsAg by Gradient Centrifugation

Cells were infected with recombinant baculoviruses containing the HBsAg gene (YM1KTs) and the supernatant fluids recovered 4 or 5 days post-infection. The cell culture supernatant fluids containing HBsAg were concentrated by precipitation with 60% ammonium sulphate. The pelleted material was resuspended in TNE (10 mM-Tris-HCl, 50 mM-NaCl, 0.1 mM-EDTA, pH 7.4) and loaded on a 20% to 60% (wt/wt) sucrose gradient in TNE buffer and centrifuged at 150,000×g for 15 h at 4° C. using an SW 41 Ti rotor (Beckman). After centrifugation, the gradients were fractionated and peak fractions containing HBsAg identified by RIA (see above), pooled and pelleted by centrifugation (Ti 50 rotor, 100,000×g for 15 h at 4° C.). The products were resuspended in $H_2O$, and samples assayed by electron microscopy. Cells infected with recombinant viruses containing HBcAg were extracted 4 days post-infection by sonication, or freezethawing three times, the products subjected to centrifugation to remove cell debris and the derived supernatant fluids centrifuged through a 30% sucrose cushion using a 42.1 rotor (Beckman) at 106,000×g for 16 h, then resuspended in TNE and purified by CsCl isopycnic centrifugation using an SW41 rotor at 160,000×g for 36 h. The gradient was fractionated and the peak fractions containing HBcAg were identified by SDS-PAGE, pooled, pelleted by centrifugation and resuspended in $H_2O$.

H. Infection of *Trichoplusia ni* with Recombinant Viruses that Express HBsAg

Groups of 10–20 fourth instar *T. ni* caterpillars grown on semi-synthetic media (Hoffman et al., 1966) were infected per os with non-occluded recombinant virus YM1KTs ($5×10^5$ p.f.a./lava) or by polyhedral inclusion bodies (PIBS) representing the recombinant VCKTs virus ($4×10^4$ PIBS/caterpillar). After 4–5 days of extrinsic incubation the visibly infected and moribund caterpillars were harvested, homogenized in 200 μl of 10 mM-Tris-HCl, pH 7.4 containing 0.02% sodium diethyldithiocarbamate. Portions (5 μl) of the homogenates were prepared for SDS-PAGE.

I. RIA for Detection and Quantitation of HBsAG

Recombinant virus derived HBsAg was measured by solid-phase radioimmune assay (AUSTRIA II; Abbott Laboratories) using the HBsAg supplied by the manufacturer (20 mg/ml) as a standard.

J. Serology

Immunofluorescence was used to detect recombinant virus-derived HBsAg and HBcAg in infected cells.

Antibodies to HBsAg (anti-HBs) in human sera were measured using a commercially available RIA (AUSAB; Abbott Laboratories) and by two solid-phase "sandwich" ELISA procedures. ELISA No. 1 used human plasma-derived HBsAg for antibody capture and detection. ELISA No. 2 used recombinant virus-derived HBsAg for antibody capture and human plasma-derived HBsAg for antibody detection. Antibodies to HBcAg (anti-HBc) were measured using two solid-phase competitive RIA. RIA No. 1 used human liver-derived HBsAg; RIA No. 2 used recombinant virus-derived HBcAg.

K. Immunofluorescence Analyses

*S. frugiperda* cells were infected with virus at a multiplicity of 1 p.fu./cell in 35 mm tissue culture dishes. At 72 h post-infection portions of 5 μl were spotted onto PTFE-coated multispot microscope slides and fixed with cold acetone for 10 min. Uninfected (control) cells were treated similarly. Sera and ascitic fluids were diluted 10-fold with PBS. 10 μl volumes of each preparation were pipetted on to one area of infected cells and one area of control cells. Slides were incubated for 30 min at 37° C. in a sealed box at high humidity. Excess antibody was rinsed from the slides with PBS, the slides were drained and any remaining liquid was removed. Appropriate conjugates were diluted in PBS containing 0.005% Evans Blue to mask non-specific (background) fluorescence. Sheep anti-human immunoglobulin-fluorescein isothiocyanate (FITC) (Wellcome Diagnostics, Dartford, UK) and goat anti-mouse IgG and IgM-FITC (TAGO, Inc., Burlingame, Calif., USA) were diluted to provide bright fluorescence with positive sera and low background staining with negative sera and on control cells. 10 μl volumes of diluted conjugate were pipetted on to each area of cells and the slides incubated at 37° C. for 30 min in a sealed box that provided a humid environment. The stained slides were rinsed and washed as before and finally rinsed for 1 min in distilled water. After drying in air the slides were examined using a fluorescence microscope.

L. RIA to Measure Anti-HBs

Antibodies to HBsAg were measured in a commercially available RIA (AUSAB) by comparison with the WHO reference anti-HBs preparation which was diluted in negative human serum to contain 100,50 and 10 International Units (IU)/L.

M. ELISA to Measure Anti-HBs

The solid-phase "sandwich" ELISA used to measure anti-HBs included a novel enhancement system developed in the Division of Microbiological Reagents and Quality Control (CPHL, Colindale). FITC-conjugated antigens or antibodies are detected by a peroxidase conjugate of the monoclonal anti-FITC antibody described by Samuel and associates (1988). In this anti-HBs assay, test antibody was sandwiched between HBsAg-coated microwells and an HBsAg-FITC conjugate. Human plasma-derived HBsAg was conjugated to FITC as described by Samuel and associates (1988) using 1 mg HBsAg and 37.5 μg FITC in 0.5 ml of 0.1M-sodium carbonate buffer, pH 9.3, containing 0.1M-NaCl. An anti-FITC peroxidase conjugate prepared by the periodate method of Wilson and Nasane (1978) was used to detect bound antigen-FITC.

Human plasma-derived HBsAg was purified from human serum and recombinant virus derived HBsAg was purified from cell culture supernatant fluids by affinity chromatography using a column of Protein-A Sepharose CL4B (Pharmacia, Uppsala, Sweden) to which monoclonal anti-HBs had been cross-linked using dimethylsuberimidate (Davies & Stark, 1970; Parkhouse, 1984). The antigen was recovered and diluted in 0.1-M-glycine-HCl buffer, pH 7.5, containing 0.1% sodium azide, to give a concentration of 1 μg/ml and used to coat polystyrene microtiter plates (Nunc-Immuno plate Maxisorp F96, A/S Nunc, Kampstrup, Denmark). 100 μl of antigen suspension were pipetted into each well and the plates incubated at room temperature for three days. They were then washed and unused binding sites blocked with 1% BSA in 0.02-M-Tris-HCl buffer pH 7.6, containing 0.1% sodium azide. Plates were stored at 4° C. until required. 100 μl of patient serum, either from HBsAg vaccinees, or from patients with a history of hepatitis B infection, as well as appropriate positive and negative controls, were added to the HBsAg coated wells and incubated at 37° C. for 1 h. The wells were washed to remove unbound material and 100 μl of human plasma-derived HBsAg-FITC conjugated buffer (PBS containing 0.05% Tween 20,5% negative human serum and 1% BSA) were added. Following incubation for 1 h at 37° C. and washing of the wells, 100 μl of monoclonal anti-FITC-peroxidase conjugate, diluted in conjugate buffer, was allowed to react with the bound HBsAg-FITC. After incubation for 1 h at 37° C. and a final washing step, a substrate solution containing hydrogen peroxide and the chromogen tetramethylbenzidine (TMB) was added (0.001 g TMB [dissolved in 100 μl dimethylsulphoxide] and 7.5 µl of 6% w/v hydrogen peri-oxide in 10 ml 0.1-M-citrate-acetate buffer, pH 6.0). The enzyme reaction was stopped after 30 min by the addition of 100 µl of 2-M-$H_2SO_4$. The absorbances of the controls and the test samples were measured at 450 nm.

N. RIA to Measure Anti-HBc

The solid-phase competitive RIA used were modifications of the method described by Cohen and associates (1981). Human liver-derived HBcAg was diluted $1.4\times10^3$-fold and recombinant virus-derived HBcAg was diluted $2\times10^5$-fold in 0.02-M-Tris-HCl buffer, pH 7.6, containing 0.1% sodium azide. Two hundred and ten etched polystyrene beads (Northumbria Biologicals, Cramlingtcn, UK) were added to 35 ml of each diluted antigen in small flasks which were shaken at room temperature for 2 h, then incubated at room temperature in the dark for a further 2–3 days. The HBcAg-beads were washed three times in PBS and stored until required at 4° C. in PBS containing 0.5% BSA and 0.1% sodium azide. 20 µl of the test sera were added to each well of an assay plate followed by 180% of $^{125}$I-labelled anti-HBc diluted in PBS containing 10% FCS. A negative serum, a strong positive and a weak positive serum served as controls and were similarly processed. Excess buffer was removed from the HBcAg-beads by blotting and one bead was added to each well. The wells were sealed and the plates incubated overnight in a humid atmosphere at room temperature. The wells were washed with distilled water using a Qwikwash (Abbot Laboratories) and then the beads were transferred to counting tubes and counted for radioactivity in a 16-well gamma-counter (NE 1600, Nuclear Enterprises, Edinburgh, Scotland, UK). Background (Bkgd) radiation was also measured. The % inhibition of the $^{125}$I-antiHBc binding was expressed as:

100-[{count-bkgd}×100+{mean negative count-bkgd}]

In these assays, "strong" positive control sera gave 94% inhibition and "weak" positive control sera gave 76% inhibition. Similar values were obtained for both the recombinant virus-derived and the liver-derived antigen. The positive cut-off value was 67% inhibition and the negative cut-off value was 50% inhibition.

(ii) RESULTS

A. Sequence Analyses of HB Virus C and PreC Genes

DNA subclones encompassing the C and preC antigens of an adw serotype of HB virus were obtained as described above. The sequences of the HBcAg and HBpcAg gene products were deduced from DNA analyses of these clones (FIG. 13). Indicated in the Figure are the methionine codons (boxed) that initiate the preC and C gene prodcuts, as well as nucleotide (open triangles) and amino acid differences (filled triangles) by comparison with the HB virus adw sequence published by Ono and associates (1983). The sequences of the indicated gene products were comparable to those published for other isolates of HB virus (see Galibert et al., 1979; Pasek et at., 1979; Valenzuela et al., 1980; Fujiyama et al., 1983; Ono et al., 1983; Bichko et al., 1985).

B. Recombinant Baculoviruses That Express HBcAg, or HBpcAg, or HBsAg

The coding sequences of the preC and C antigens of HB virus were inserted into the AcNPV transfer vector pAcYM1 (Matsuura et al., 1987) as described above (FIG. 9). The derived recombinant transfer vectors (pAcYM1KTpc, pAcYM1KTc) were analysed by restriction endonuclease digestion and the junction sequences determined as shown in FIG. 9. Following cotransfection with infectious AcNPV DNA, recombinant baculoviruses were obtained (YM1KTpc, YM1KTc), plaque purified and high titred virus stocks obtained. The levels and identities of the 24.6 kilodalton HBpcAg and 21.4 kilodalton HBcAg were determined by the incorporated of labelled methionine (FIG. 14, left-hand panel) and by Western analyses (FIG. 14 right-hand panel). Essentially all the HBcAg and HBpcAg antigen was cell associated. Electron micrographs of HBcAg extracted from infected cells and purified by CsCl gradient centrifugation are shown in FIG. 15A. From analyses of stained protein gels of the gradient purified HBcAg, by comparison with known amounts of bovine serum albumin, the yield of purified HBcAg was determined to be of the order of 5 mg per liter of $1\times10^9$ infected cells.

Using small volume cell cultures (e.g. 35 mm dishes), the level of HBsAg synthesis by the recombinant baculovirus HBsYK14 (Kang et al., 1987) has been reported to be equivalent to 1.5 mg per $10^9$ infected cells. In large culture volumes (100–1000 ml), expression levels of the order of 0.3–0.5 mg per $10^9$ infected cells are obtained with the same virus. The reason for this difference in expression level is not known. In order to improve this the HBS gene was transferred from the pAcRP6 vector to the pAcYM1 vector since higher expression has been observed with the latter for a variety of gene products (see Matsuura et al., 1987). In an initial study, the HBsAg gene was recovered from the transfer vector pAcRP6-HBsYK14 (Kang et al., 1987) by BamHI digestion and inserted directly into the BamHI site of transfer vector pAcYM1. The derived transfer vector was used to prepare a recombinant virus and the level of HBsAg synthesis was measured. The data obtained (not shown) indicated that the level of expression was equivalent to 0.3 mg per $10^9$ infected cells and similar to that of the recombinant HBsYK14 run in parallel.

One reason for the low expression level could have been the presence of some 100 nucleotides of the HB genome upstream of the HBsAg coding region (i.e., between the HB BamHI site and the HBsAg translation initiation ATG). In view of this, the transfer vector pAcYM1KTs was prepared (FIG. 10). This vector was used to produce a recombinant virus (YM1KTs). The presence of HBsAg in the supernatant fluids (containing the secreted 22 nm HBsAg particles) and residual HBsAg in cell lysates was measured. The yield of HBsAg (cell associated and in the supernatant fluids) was estimated from the RIA assays to be of the order of 0.3 mg per liter of $1\times10^9$ infected cells by 5 days post-infection (FIG. 16). This level of HBsAg expression was no different to that obtained with the other recombinants (e.g. HBsYK14). The incorporation of labelled methionine into the cell-associated HBsAg was also measured (FIG. 14, see Kang et al., 1987). Electron micrographs of HBsAg purified from the supernatant fluids by sucrose gradient centrifugation are shown in FIG. 15B.

C. Recombinant Baculoviruses That Coexpress HBcAg and HBsAg

A sequence containing the polyhedrin promoter, the HBsAg gene and the polyhedrin transcription termination signal was recovered from the HBsAg transfer vector pAcYM1KTs by AccII digestion (FIG. 11). It was inserted into the EcoRV sites of the transfer vectors pAcYM1KTpc and pAcYM1KTs in order to make dual recombinant vectors (FIG. 12). The recombinant vectors were characterised and the vector with the HBsAg gene in the opposite orientation to the C gene (pAcVCKTspc see FIG. 11) were used to derive recombinant viruses by cotransfection of S. frugiperda cells in the presence of infectious AcNPV DNA. The recombinant virus VCKTsc were recovered, plaque purified and grown into high titred virus stock. The antigens made by the VCKTsc recombinant were analysed. The synthesis of HBcAg by the VCKTsc recombinant was demonstrated by the incorporation of labelled methionine and by Western analyses (FIG. 14). The level of synthesis of HBcAg was essentially similar to that obtained with the recombinant YM1KTc.

The synthesis and secretion of HBsAg by cells infected with the dual recombinant VCKTsc and the residual cell-associated HBsAg were determined by ELISA assays (FIG. 14). Based on the RIA assays, the total yield of HBsAg was estimated to be of the order of 0.4 mg per liter of $1\times10^9$ infected cells by 5 days post-infection (FIG. 16), slightly higher than that obtained with the single expression recombinant virus, YM1KTs, analysed in parallel. The level of secreted HBsAg (FIG. 16) was almost twice that obtained with the recombinant YM1KTs, although the cell associated HBsAg was essentially the same. Overall, though, the level of HBsAg synthesis represented only a small fraction of the amount of HBcAg synthesis.

D. Recombinant Baculoviruses That Coexpress HBsAg and AcNPV Polyhedrin Protein

The sequence containing the polyhedrin promoter, the HBsAg gene and the polyhedrin transcription termination signal was recovered from the HBsAg transfer vector pAcYM1KTs by AccII digestion (FIG. 12). It was inserted into the EcoRV site of the EcoRI "I" fragment in order to make a dual recombinant vector that contained the HBsAg gene in addition to the AcNPV polyhedrin gene. The recombinant vectors were characterised and those with the HBsAg gene in the opposite orientation to the polyhedrin gene (pAcVCKTs FIG. 12) were used to derive recombinant viruses by cotransfection of *S. frugiperda* cells in the presence of infectious AcNPV DNA. The proteins made in infected *S. frugiperda* cells by recombinant VCKTs are shown in FIG. 14 by comparison with an AcNPV infection so that the AcNPV polyhedrin protein could be identified. Although for the latter only small amounts of polyhedrin were made (m.o.i. that was used was <1 p.f.u./cell), the data served to identify the polyhedrin protein in the VCKTs infected cells. As in the other recombinants that contained the HB S gene, the synthesis of HBsAg was a minor component of the labelled proteins. From RIA it was estimated to represent some 0.4 mg per liter of $1\times10^9$ infected cells by 5 days post infection.

E. Levels of Synthesis of HB Proteins in Recombinant Virus Infected *S. frugiperda* cells In FIG. 17 are shown the profiles of stained proteins recovered from cells infected with the single expression recombinant viruses YM1KTc, YM1KTpc, and YM1KTs, or the dual expression recombinants, VCKTsc and VCKTs, by comparison with an AcNPV infection end mock virus infected cells. The AcNPV and VCKTs infections were initiated at multiplicities of ca 1 p.f.u./cell (accounting for the low levels of polyhedrin protein), the other viruses at 10 p.f.u./cell, and the proteins recovered 2 days post-infection. It was evident that for viruses containing the HB C gene, the HBcAg was present in the cell extracts in substantial quantities (estimated visually to be ca 40% of the total protein in the cell extracts). The preC antigen was observed in lower amount (estimated ca 5–10% of the stained proteins). Between multiplicities of 1–10 p.f.u./cell essentially similar results to those shown in FIG. 17 were obtained for recombinants containing either the HB C, or the HBpC gene.

Despite the fact that the HBsAg was located in a position in the gel where a cellular protein migrated (see FIG. 17, Mock track), it could be visualized as an enhanced band in the stained gels, although in an amount considerably lower than the amount of HBcAg. Between multiplicities of 1–10 p.f.u./cell essentially similar levels of cell-associated HBsAg were observed by 2 days post-infection, although for the VCKTs virus there were enhanced levels of polyhedrin protein at the higher multiplicities (estimated to be ca 40% of the cellular protein, see FIG. 14). Even at the higher multiplicities, it was estimated that the cell-associated HBsAg represented no more than ca 2% of the stained proteins.

F. Immunofluorescence Using Recombinant Virus Infected Cells Expressing HBcAg and HBsAg to Identify Human Antibodies to Those Antigens Human sera were provided by the Virus Reference Laboratory of the CPHL, Colindale. Eight human sera that were strongly positive for antibody to HBcAg and negative for antibody to HBsAg in radio-immunoassays were used to stain the slides. Every serum gave good fluorescence on the recombinant VCKTcs virus infected insect cells (FIG. 18, left-hand panel), but not reaction to control, uninfected cells (FIG. 18, right-hand panel), indicating that by this procedure the antigens in the infected cells were suitable substrates for the detection of human antibodies to HBcAg.

Human vaccinee sera with high levels of antibody to HBsAg (up to 500 International Units [IU] per liter), but which contained no anti-HBcAg as judged by the appropriate RIA, gave no fluorescence on the same recombinant virus infected cells. The presence of HBsAg in these virus infected cells was confirmed, however, using a mouse monoclonal anti-HBsAg, giving good fluorescence (FIG. 18, center panel). It was concluded that the cell-associated HBsAg in the virus infected cells was not adequate for identifying such levels of human antibodies to HBsAg.

G. ELISA Assays Using Purified Recombinant Virus Derived HBsAg to Identify Human Antibodies to HBsAg Eighty-eight sera sent to the Virus Reference Laboratory for anti-HBsAg determination and ninety-one sera from HBsAg-negative blood donations (North London Blood Transfusion Center, Edgware, UK) were tested by RIA and ELISA. The RIA used a non-recombinant HBsAg from Abbott Laboratories. The ELISA No. 1 assay used the human plasma derived HBsAg for both antibody capture and detection. The ELISA No. 2 assay used the recombinant HBsAg purified as described in Methods for antibody capture and a human plasma derived HBsAg for detection. The results were compared to positive control sera prepared by dilution in normal human serum of World Health Organisation (WHO) anti-HBsAg reference serum (RIA), or Blood Products Laboratory (BPL, Elstree, UK) anti-HBsAg reference serum (ELISA). The control sera contained 10,50 and 100 IU/liter of anti-HBsAg antibody. There was good agreement between the tests using the two different antigen sources for antibody capture as shown in Table 1.

H. Competitive RIA Using Purified Recombinant Virus Derived HBcAg to Identify Human Antibodies to HBcAg One hundred and fifty sera sent to the Virus Reference Laboratory (Colindale) for anti-HBcAg determination were tested by competitive RIA using either the recombinant virus derived HBcAg, or human liver derived HBcAg.

Six of the sera tested gave "weak positive" reactions with one test but "negative" reactions with the other (see above and Table 2). Two sera gave positive reaction in the RIA using liver derived material and a negative reaction using the recombinant antigen. The comoetitive RIA with human liver-derived HBcAg is known to give some false positive results—possibly due to the serum reacting against liver proteins. In view of this the agreement between the two tests was considered excellent, however, many more sera will have to be tested in the RIA (or by ELISA) with the recombinant virus derived HBcAg to determine the suitability and specificity of such tests.

I. Expression of HBsAg in *T. ni* larvae

When the single expression vector for HBsAg (recombinant YM1KTs) was used to infect fourth instar larvae of *T. ni* ($1-2 \times 10^5$ p.f.u./larva) it was found that the quantity of HBsAg in moribund larvae was of the order of 1–2 µg per larva. However at this late larval development stage only 30% of the larvae became infected. Reproducible infection was obtained using earlier instar larvae, however the yields of antigen were correspondingly lower (<0.1 µg per larva). The use of higher titers of virus to circumvent the problem with fourth instar larvae was not considered practicable without concentrating the virus. Stock virus titers were usually of the order of $10^{7-7.7}$ p.f.u./ml tissue culture fluids.

It has been demonstrated that occluded AcNPV are more effective and reproducible at establishing infections in *T. ni* larvae than non-occluded AcNPV (See Example 1). Individual fourth instar *T. ni* larvae were therefore infected with $4 \times 10^4$ PIBS representing the occluded recombinant VCKTs (see above. All the larvae became infected. The levels of HBsAg obtained in these larvae were of the order of 2–4 µg per larva.

J. Electron Microscope Analyses of Cells Infected with Recombinants that Express the HBcAg In view of the amounts of HBcAg synthesized in *S. frugiperda* cells infected with the recombinant virus YM1KTc, an examination of electron micrographs of cells infected with the virus was undertaken (FIG. 19). Numerous spherical particles were evident in the cells, primarily in the vicinity of the cell nucleus. The sizes of the particles were comparable to those of gradient purified HBcAg (See FIG. 15).

SUMMARY

In order to demonstrate the feasibility of constructing multiple expression vectors that can make large quantities of different foreign proteins in the same cell, we have prepared a baculovirus plasmid replicon, pAcVC2, that contains the complete coding regions of both the AcNPV polyhedrin gene and the LCMV-N gene. Each gene was constructed so that it had its own copy of the AcNPV polyhedrin promoter and transcription termination sequences, although the LCMV-N gene was positioned in an opposite orientation to that of the polyhedrin. The derived plasmid was co-transfected with a polyhedrin-negative viral DNA into *S. frugiperda* cells and recombinant viruses with a polyhedrin-positive phenotype were isolated.

Upon analysis by a variety of biochemical procedures it was shown that recombinant viruses, such as VC2, produced both the LCMV-N protein and polyhedrin protein simultaneously and in a regulated fashion (i.e., as a major late proteins). The two gene products represented a substantial proportion of the total cellular protein. Such results are significant since they demonstrate that a recombinant baculovirus derived from a plasmid replicon containing a duplicated polyhedrin promoter as illustrated in FIG. 1 (e.g., pAcVC2) is capable of making two gene products in large quantities.

One skilled in the art will also recognize that plasmid replicons can be constructed which comprise sequences directing expression of the polyhedrin gene and sequences comprising a PES including a transcriptional promoter, a single unique restriction site for introduction of a gene which is native or foreign to the expression vector wherein the introduced gene is under the control of the said transcriptional promoter, and a transcriptional termination site. Said replicons can be constructed de novo, or can be created by replacing only the LCMV-N gene of pAcVC2 with a unique restriction enzyme site. These plasmid replicons would afford insertion of a single foreign gene, and result in plasmid replicons comprising polypeptide expression sequences directing simultaneous expression of the polyhedrin protein and the foreign protein. Said plasmid replicons would facilitate construction of baculovirus expression vectors that can be used to create polyhedrin-positive recombinant baculoviruses expressing said foreign genes. Moreover, plasmid replicons comprising sequences directing polyhedrin gene expression and a unique restriction site can be used to construct recombinant baculovirus expression vectors containing unique restriction sites suitable for subsequent insertion of foreign genes directly into said baculovirus expression vectors.

By constructing a new vector in which the pAcVC2 polyhedrin gene is replaced by an alternative foreign gene and co-transfecting cells with the derived plasmid in the presence of VC2 DNA it should be possible to obtain recombinant polyhedrin-negative viruses that express both foreign proteins simultaneously. Since the level of expression by the polyhedrin transcriptional machinery is related to the representation of the sequences upstream of the polyhedrin ATG (Matsuura et al., 1987), it will be possible to regulate the level of the different foreign genes that are expressed by manipulation of those sequences.

As far as could be ascertained by the experiments that were undertaken, (Northern analyses of the LCMV-N and polyhedrin gene mRNA levels in VC2 virus infected cells) there was not a significant difference between the mRNA levels or expression in molar terms of the two genes nor, as far as could be ascertained from parallel analyses, was there a significant difference in the level of polyhedrin mRNA between cells infected with the VC2 virus by comparison with AcNPV.

Electron micrographs of VC2 virus infected *S. frugiperda* cells have shown that intracellularly polyhedrin assembles to form nuclear inclusion bodies indistinguishable from those found in wild-type AcNPV infections and that the LCMV-N protein aggregates to form cytoplasmic inclusion bodies. Furthermore, VC2 virions are occluded within the polyhedral inclusion bodies. The use of insects (specifically the caterpillar *T. ni*) that are susceptible to baculovirus infection to produce recombinant viral proteins has been demonstrated by various investigators (Maeda et al., 1985; Overton et al., 1987). In natura, infection of susceptible caterpillars proceeds by dissolution of the polyhedral inclusion body in the alkaline pH of the insect midgut to liberate virions which then infect the susceptible midgut cells. In the subsequent stages of a caterpillar infection, non-occluded virions are budded through the plasma membrane of the midgut cells into the haemolymph and hence propagate the infection to other cells and tissues of the insect. This systemic infection subsequently yields large quantities of occluded viruses that are important for the persistence of the baculovirus in the environment (hence subsequent infection cycles in other insect generations). Thus, the polyhedral inclusion body plays an important role in the natural infection of caterpillars by baculoviruses. This role is not emulated to the same efficiency by polyhedrin-negative viruses, as indicated by the reduced larval infections obtained using the non-occluded VC2 virus. Infection of *T. ni* caterpillars with the VC2 derived polyhedra produced a potent infection with the concomitment production of substantial amounts of LCMV-N protein.

The preparation of recombinant baculoviruses that produce polyhedrin and one (or more) foreign gene product simultaneously should circumvent some of the low infectivity problems associated with the use of polyhedrin-negative recombinant baculoviruses in the exploitation of caterpillars to produce large quantities of a protein product efficiently and cost effectively. Similarly the availability of genetically engineered baculoviruses with the capacity to express polyhedrin and a gene product toxic to caterpillars (or a gene that will produce other deleterious effects to the animal) may lead to the production of more efficacious baculovirus insecticides with a level of infectivity and persistence in the environment akin to that of the natural wild-type virus, allowing long-term pest protection (see Bishop, 1986). Based on the results described here the possibility of preparing and exploiting other multiple expression systems based on baculoviruses (or other vectors) is manifest, either by taking the route followed herein, or by placing the requisite regulatory gene machinery of the same or a genetically compatible organism (or virus) into other regions of a genome.

The plasmid replicon pAcVC2 has been modified by replacing the LCMV-N gene and polyhedrin gene with unique restriction enzyme sites that will allow any two foreign genes to be inserted and ultimately expressed simultaneously at the recombinant virus level. The derived general purpose replicon pAcVC3 with two PESs organised in non-overlapping sequences on opposite strands of DNA will allow foreign genes to be inserted into the plasmid by virtue of the unique BglII amd BamHI restriction sequences. (See FIG. 8 and Example 1 (ii) MATERIALS AND METHODS (j) Construction of pAcVC3).

The hepatitis B (HB) virus sequences coding for the preC, or C antigens (HBpcAg, HBcAg) have been inserted into the baculovirus plasmid transfer vector, pAcYM1, such that the HB viral sequences are under the control of the polyhedrin promoter of *Autographa californica* nuclear polyhedrosis virus (AcNPV). *Spodoptera frugiperda* cells infected with either of the derived recombinant plasmids in the presence of infectious AcNPV DNA yielded recombinant, polyhedrin-negative, viruses that expressed high levels of the respective HBpcAg, or HBcAG (representing ca 5–10% [HBpcAg] and ca 40% [HBpcAg] of the stained cellular proteins respectively). The particulate 27 nm HBcAg have been purified to homogeneity from infected cell extracts by density gradient centrifugation. Dual expression transfer vectors containing the HBcAg gene sequences and the coding sequences of the HB viral S antigen (HBsAg), (each gene under its own copy of the polyhedrin promoter) have also been constructed and used to derive recombinant viruses. The recombinant with the HBVC and S genes expressed high levels of the HBcAg (ca. 40% of the cellular proteins) at the same time as low levels of the HBsAg (ca. 2% of the stained cellular proteins). Dual expression, occluded, recombinant baculoviruses that make HBsAg as well as AcNPV polyhedrin protein have been prepared that are highly infectious for Trichoplusia ni caterpillars, allowing reproducible preparation of the antigen in a cost-effective manner.

Using radioimmunoassays (RIA) and ELISA, the recombinant HBcAg (RIA) and HBsAg (ELISA) have been used to identify human antibodies to HB virus with results that compare favourably with the data obtained with non-recombinant antigens.

DEPOSITS

A sample of plasmid pAcVC3 in *E. coli* MC1061 has been deposited on 7th Aug., 1987 under accession number NCIB12516 with the National Collection of Industrial and Marine Bacteria, 135 Abbey Road, P O Box 31, Aberdeen AB9 8DG.

A sample of recombinant virus VC4 has been deposited on 10th Aug., 1987 under accession number 87081001 with the National Collection of Animal Cell Cultures PHLS, Centre for Applied Microbiology & Research, Porton Down, Salisbury, Wiltshire SP4 09G.

A sample of plasmid pAcYM1KTs in *E. coli* JM105 has been deposited on 25th Jul., 1988 under accession number NCIB40033 with the National Collection of Industrial and Marine Bacteria, 135 Abbey Road, P O Box 31, Aberdeen AB9 8DG.

A sample of plasmid pAcVCKTs in *E. coli JM*105 has been deposited on 21st Jul., 1988 under accession number NCIB40028 with the National Collection of Industrial and Marine Bacteria, 135 Abbey Road, E C Box 31, Aberdeen AB9 8DG.

A sample of plasmid pACVCKTsc in *E. coli* JM105 has been deposited on 21st Jul., 1988 under accession number NCIB40029 with the National Collection of Industrial and Marine Bacteria, 135 Abbey Road, P O Box 31, Aberdeen AB9 8DG.

A sample of plasmid pAcVCKTspc in *E. Coli* JM105 has been deposited on 21st Jul., 1988 under accession number NCIB40030 with the National Collection of Industrial and Marine Bacteria, 135 Abbey Road, P O Box 31, Aberdeen AB9 8DG.

A sample of plasmid pAcYM1KTs in *E. coli* JM105 has been deposited on 21st Jul., 1988 under accession number NCIB40031 with the National Collection of Industrial and Marine Bacteria, 135 Abbey Road, P O Box 31, Aberdeen AB9 8DG.

A sample of plasmid pAcYM1KTpc in *E. coli* JM105 has been deposited on 21st Jul., 1988 under accession number NCIB40032 with the National collection of Industrial and Marine Bacteria, 135 Abbey Road, P O Box 31, Aberdeen AB9 8DG.

Example 3

High-Level Expression of Five Foreign Genes by a Single Recombinant Baculovirus (i) INTRODUCTION This Example is directed to the high level expression of five foreign genes by a single recombinant baculovirus.

The majority of gene expression vectors are designed to express a single foreign protein. However, to obtain reproducible and maximum yields of a multiprotein product, e.g., a virus-like particle, it is often important that the proteins are expressed at optimal ratios.

The co-expression of several proteins using multiple gene expression vectors provides the desired expression of several foreign proteins in every infected cell. In such cases the ratio of expression can be controlled and adjusted to provide an optimal ratio by manipulating the promoters to control the levels of gene transcription and hence the protein expression. Due to the vicissitudes of the translation process, optimal ratios of expressed proteins can only be achieved empirically.

Dual gene expression vectors have greatly facilitated research on the reconstruction of complex protein structures, such as virus core-like particles and virus-like particles (French and Roy, 1990; French et al., 1990; Weyer and Possee, 1991). Recently, triple (pAcAB3) and quadruple (pAcAB4) baculovirus transfer vectors have been developed which synthesize three or four foreign proteins (respectively). Also, bluetongue virus virus-like particles have been produced using a single quadruple recombinant baculovirus (Belyaev and Roy, 1993). This Example describes the procedure and protocols required for synthesizing high levels of five bluetongue virus proteins using a single quintuple recombinant baculovirus. This Example further demonstrates the reproducible ratios of five proteins synthesized by a single recombinant virus which is in contrast to the variable amounts of products synthesized by co-infection of different recombinant viruses each producing one foreign protein.

(ii) MATERIALS, METHODS AND CALCULATIONS (a) Mathematical Analyses of Foreign Protein Expression Using Co-Infections Wild-type *Autographa californica* nuclear polyhedrosis virus (AcNPV) producing the viral polyhedrin protein, and single recombinant AcNPV viruses synthesizing either *Escherichia coil* β-galactosidase, or bluetongue virus VP6, or VP7, or NS1 proteins were chosen for the co-infection experiments. Each virus abundantly synthesizes a non-secreted protein. This facilitates the estimation of the production level of the proteins in co-infected cells.

To investigate the production levels in Sf cells co-infected with 2 or 5 viruses, after a period of virus adsorption, the cells were diluted, mixed with uninfected cells, and plated to form monolayers; after cell attachment, the cells are incubated under agar. Individual virus plaques (infectious centers) were picked and used to infect monolayer cultures of *S. frugiperda* (Sf) cells and the production of the foreign proteins studied by SDS-PAGE analysis.

The analysis of the protein synthesis/production in single or multiple virus infections is shown in FIG. 20. FIG. 20, Panel A shows the results from single virus infections and co-infection with two viruses. The recombinant viruses, each expressing a single foreign gene (either β-galactosidase (β-gal), or bluetongue virus NS1, or VP6, or VP7), and wild type AcNPV to express polyhedrin, were used to infect Sf cells as indicated. FIG. 20, Panel B shows co-infection with five viruses. Sf cells were co-infected with recombinant baculoviruses at a multiplicity of 5 FPU per cell. Each was expressing a single gene as well as AcNPV. The infected cells were diluted, mixed with uninfected cells to form monolayers, covered with agar and incubated at 28° C. for 3 days. Individual plaques (infectious centers) were picked, viruses were recovered from such plaques monolayers of Sf cells were infected with the recovered viruses. Cells were harvested 3 days post-infection, washed with phosphate-buffered saline, and lysed at 4° C. in 50 mM Tris hydrochloride (pH 8), 150 mM NaCl-0.5% Noniodet P-40. Protein dissociation buffer (10% β-mercaptoethanol, 10% sodium dodecyl sulfate [SDS], 25% glycerol, 10 mM Tris hydrocloride [pH 6.8], 0.02% bromphenol blue) was added to the samples, and the mixtures were incubated at 100° C. for 5 min. Proteins were separated by SDS-PAGE and stained with Coomassie brilliant blue. As controls, the expression from uncloned cells under the same condition is shown foDr either the five virus co-infection (*), or an infection with only the lacZ recombinant virus (β).

The results showed that single virus infections synthesized all 5 foreign proteins (FIG. 20, Panel A). When the cells were co-infected with 2 viruses, both of the expressed proteins (β-galactosidase and polyhedrin) were produced in the majority of samples analyzed. Polyhedrin alone was only detected in one case (FIG. 20), Panel A, right hand lane). However, when co-infecting with 5 viruses (FIG. 20, Panel B), one or more proteins were not detected in most of the samples. Additionally the ratio of expression of the individual proteins was not constant between samples. For most samples, the production level of one or more proteins was much lower than in other samples.

In single virus infections, individual cells may receive different numbers of virus particles. If virus particles are distributed randomly across cells, at a given m.o.i. ($\mu$), the proportion (P) of cells receiving a certain number (x) of particles will follow a Poisson distribution:

$$P(x) = \frac{e^{-\mu}\mu^x}{x!}$$

For co-infections, it may be assumed that each virus type is distributed between cells independently. The percentage of cells lacking one or more virus types is low (e.g., 1.3%, 2%, 2.5% and 3.5%) for 2, 3, 4 or 5 virus co-infections each at a m.o.i. of 5. However, if the optimal ratio of synthesized proteins is provided by an ecqual ratio of infecting viruses, a minority of cells receive such ratios as the numbers of virus types involved are increased. For example, the proportion of cells actually receiving three different co-infecting viruses, at an equal ratio, P(1:1:1), may be calculated as:

$$P(1:1:1) = \sum_{r=1}^{\infty} \frac{e^{-(\mu_1+\mu_2+\mu_3)}\mu_1^r\mu_2^r\mu_3^r}{r!r!r!}$$

Theoretically with 2, 3, 4 or 5 virus types each at a m.o.i. of 5, the percentage of cells receiving an equal ratio of the viruses are 12.78%, 1.88%, 0.29% and 0.05%, respectively. Most cells will receive more of a particular virus type and lesser or more numbers of the other viruses. As a consequence, there is likely to be an uneven (or disproportionate) synthesis of the individual proteins in the cells. Thus, the greater the number of virus types that are involved in a co-infection, the smaller the probability that individual cells will receive all of them at an equal ratio. Hence, the smaller number is the percentage of the cell population operating at this level of efficiency. This is, of course, not apparent by analyses of the total protein production by the population of cells, but is indicated by the infectious center assays (FIG. 20, Panels A and B).

Thus, an inherent disadvantage of co-infections is that it is impossible to control the ratios at which individual cells are infected with more than one virus. As a consequence, it is not possible to control the ratio of multiple foreign protein synthesis in individual cells. To overcome this difficulty, multiple gene expression vectors have been developed which allow for the synthesis of up to five proteins using a single recombinant baculovirus.

(b) Construction of Quintuple Recombinant Baculoviruses

Quintuple recombinant baculoviruses were constructed initially using a quadruple plasmid transfer vector, pAcAB4, to integrate four foreign genes into the polyhedrin locus of AcNPV DNA (See FIG. 21, Panel A). FIG. 21, Panel A presents a schematic diagram showing the sequential steps utilized for generating the quintuple recombinant baculovirus. Subsequently a single gene transfer vector, pAcUW1, was employed to integrate a fifth gene into the p10 locus of the derived recombinant baculov:irus DNA (Weyer et al., 1990).

Bluaetongue virus genes coding for virus structural and non-structural proteins were used for the construction of the quintuple recombinant baculovirus. Genes coding for the bluetongue virus VP4, VP6, NS1 and NS2 proteins (Roy and Gorman, 1990) were cloned into the pAcAB4 vector to produce a recombinant transfer vector designated pAcAB4.VP6/NS1/NS2/VP4. For the construction of recombinant plasmid transfer vectors, bluetongue virus DNA fragments were excised from the single gene transfer vectors by digesting with BamHI as described previously (Roy et al., 1990; Maniatis et al., 1982, Thomas et al., 1990). To achieve this BamHI fragments, coding regions for VP6 and VP4 were cloned (respectively) into the BamHI and BglII sites of the pAcAB4 vector (see FIG. 21, Panel A). BamHI fragments coding for NS and NS2 wre first subcloned into the BAMHI site of pUC19, excised using SmaI and XbaI and then cloned respectively into SmaI-SpeI and XbaI-StuI sites of the pAcAB4 quadruple transfer vector. As a result, a plasmid transfer vector, pAcAB4.VP6/NS1/NS2/VP4, for insertion of the four bluetongue virus genes into the polyhedrin locus of AcNPV DNA, as well as intermediate constructs pAcAB4.VP6/0/0/0. AcAB4.VP6/0/0/VP4 and pAcAB4.VP6/NS1/0/VP4, were obtained (see FIG. 21, Panel A). Sf cells were transfected with a mixture of pAcAB4.VP6/NS1/NS2/VP4 DNA and linearized BacPAK6 baculovirus DNA (described elsewhere (Kitts and Possee, 1993)). Recombinant plaques with a white phenotype were isolated and the quadruple gene recombinant baculovirus AcBT-VP6/NS1/NS2/VP4 was propagated.

Integration of the fifth bluetongue virus gene into the p10 locus of AcNPV was achieved in two steps (FIG. 21, Panel B). First, *E coli* lacZ gene was integrated into the p10 site of AcBT-VP6/NS1/NS2/VP4 to provide the recombinant virus AcBT-VP6/NS1/NS2/VP4/lacZ. The progeny virus plaques were stained blue on the exposure to the β-galactosidase substrate, X-Gal. Second, the lacZ gene in this quintuple recombinant baculovirus was substituted for the bluetongue virus gene coding for VP7. To insert the fifth gene into the p10 locus of AcNPV DNA, a bluetongue virus DNA fragment coding for VP7 was excised with BamHI enzyme from a previously described single gene transfer vector and cloned into the BGlII site of pAcUW1, a p10 insertion vector (Weyer et al., 1990; Oldfield et al., 1990). Recombinant baculoviruses were constructed from pAcAB4.VP6/NS1/NS2/VP4 as well as the intermediate plasmid constructs as described previously (Belyaev and Roy, 1993; Kitts and Possee, 1993). The AcBT-VP6/NS1/NS2/VP4/lacZ virus DNA was linearized within the lacZ gene sequence using the restriction enzyme Bsu 361 (FIG. 21, Panel B). The linearized virus DNA was co-transfected with pAcUW1-VP7 plasmid transfer vector DNA and recombinant plaques with a white phenotype were selected. The resulting quintuple recombinant baculovirus was designated AcBT-VP6/ns1/NS2/VP4/VP7 (See FIG. 21, Panel B).

(iii) RESULTS

Analysis of Protein Expression by a Quintuple Recombinant Baculovirus

*S. frugiperda* (Sf) cells were infected with the recombinant baculoviruses described above and the synthesis of foreign proteins was analyzed by SDS-PAGE. Synthesis of foreign proteins by quintuple recombinant baculoviruses is presented in FIG. 22. FIG. 22 summarizes the results obtained with the quintuple recombinant baculovirus and the intermediate constructs.

Briefly, the experimental protocol for FIG. 22 is as follows: Sf cells were infected with the recombinant baculoviruses or with wild-type AcNPV at a multiplicity 5 PFU per cell. Cells were harvested 3 days post-infection. Proteins were separated by 10% SDS-PAGE and stained with Coomassie brilliant blue.

Lane 1—Single recombinant baculovirus synthesizing bluetongue virus VP6 (Roy et al., 1990);

Lane 2—Wild type AcNPV, polyhedrin band indicated by asterisk;

Lanes 3–5—Recombinant baculoviruses generated with the intermediate transfer vector constructs pAcAB4.VP6/0/0/0. pAcAB4.VP6/0/0/VP4 and pAcAB4.VP6/NS1/0/VP4, respectively;

Lane 6—Quadruple recombinant baculovirus AcBT-VP6/NS1/NS2/VP4;

Lane 7—Quintuple recombinant baculovirus AcBT-VP6/NS1/NS2/VP4/lacZ;

Lane 8—Quintuple recombinant baculovirus AcBT-VP6/NS1/NS2/VP4/VP7;

Lane 9—Recombinant baculovirus BacPAK6 (Kitts and Possee, 1993);

Lane 10—Dual recombinant baculovirus synthesizing VP3 and VP7 (French and Roy, 1990).

The results from this experiment demonstrated that all five foreign genes were expressed at a high level (FIG. 22, lanes 7,8) as detected by Coomassie blue stained PAGE. As shown in lanes 3–8, the introduction of the additional genes did not significantly reduce the level of expression of the previously cloned genes. The quintuple recombinant baculovirus show no signs of genetic instability during at least six subsequent passages (data not shown). This Example yielded a fixed ratio of bluetongue virus protein synthesis that was similar to the ratio of these proteins produced in native bluetongue virus infections (Roy and Gorman, 1990). As seen in FIG. 22, the non-structural proteins NS1 and NS2, as well as the major structural protein VP7, were produced abundantly; the minor structural proteins VP4 and VP6 were less prominent.

(iv) CONCLUSIONS

The production of proteins at a required ratio in an individual cell is critical for the synthesis of multi-component structures within cells. Since the synthesis of proteins in a single cell is difficult to analyze directly, cell cultures were infected with a pool of viruses and the cells were plated with feeder cells to recover plaques of the expressed viruses (infectious centers) which were analyzed for their ability to synthesize proteins. The results indicated that production levels of the proteins in the secondary cultures varied according to the plaque selected. It was observed that proteins were lacking or under-represented in some samples but not in others, suggesting that the variation was a result of differences in the virus ratios during co-infection. The probability that some cells have not been infected with a virus is low. According to the Poisson distribution, it is only 0.3% at an m.o.i. of 5 (which was used in these experiments). Since it is impossible to provide a single ratio of co-infecting viruses for the whole cell population, unequal infection and consequential variation in protein synthesis is an inherent feature of co-infections.

Furthermore, biological and temporal factors may also contribute to variations in infection and protein synthesis. For example, during adsorption and entry, virus particles may compete for receptors. Such problems are eliminated if all of the required protein products are synthesized using a single recombinant virus.

As previously reported, triple and quadruple baculovirus expression vectors have been developed (Belyaev and Roy, 1993). This Example presents the construction and results of quintuple baculoviruses expressing five foreign genes to high levels. As co-infection of a cell with two viruses is generally successful (see FIG. 20, Panel A), the inventors predict that up to 10 foreign genes could be expressed using two quintuple baculoviruses. Such recombinant systems would be ideal for reconstruction of many multi-component protein systems, including various complex enzymes, such as yeast RNA polymerase II (10 genes), vaccinia virus RNA polymerase (9 genes), complex receptors such as a T-cell receptor, and operons such as the *Helicobacter pylori* urease operon (9 genes), or the complete enzymatic chains for the synthesis of certain antibiotics (Woychik and Yong, 1990; Ahn et al., 1992; Janeway, 1992; Cussac et al., 1992; Malpartida et al., 1984).

(v) SUMMARY

Co-infection with several viruses is often used to achieve simultaneous expression of several proteins. From co-infections involving several viruses, the ratio of proteins synthesize in individual cells can be very variable. This is disadvantageous where proteins are needed to interact to provide a maximum yield of a complex product. Multiple gene-expression vectors offer an alternative to co-infections. Multiple gene-expression vectors enable reproducible ratios of products to be provided in each infected cell. Until recently, multi gene-expression vectors have only been developed to make two proteins simultaneously. Example 3 describes the generation of a single recombinant baculovirus synthesizing up to five foreign proteins with a fixed ratio comparable to the ratio of the native proteins synthesis.

TABLE 1

Anti-HBs levels in human sera tested by RIA and ELISA

| | RIA [ELISA #1] | | | | |
|---|---|---|---|---|---|
| ELISA #2 | negative | <10 IU/L | 10–50 IU/L | 50–100 IU/L | >100 IU/L |
| negative | 5 [90] | | | | |
| <10 IU/L | [1] | 1 | | | |
| 10–50 IU/L | | | 5 | | 1 |
| 50–100 IU/L | | | | 3 | |
| >100 IU/L | | | | 1 | 72 |

Human antibody titers to HBsAg were determined using human plasma derived HBsAg for antibody capture (and detection) and reference anti-HBs from WHO in RIA assays, or from BPL (Elstree, UK) in [ELISA #1] assays. The data were compared to the human antibody titers determined using the recombinant HBsAg for antibody capture (and human plasma derived HBsAg for detection) and reference antibody from BPL in ELISA #2 assays.

TABLE 2

Anti-HBc analyses of human sera using RIA and liver or recombinant derived antigen

| | RIA #1 | | |
|---|---|---|---|
| RIA #2 | negative | weak positive | strong positive |
| negative | 76 | 4 | 2 |
| weak positive | 2 | | |
| strong positive | | | 66 |

Human antibody titers to HBcAg were determined using liver (RIA #1) or recombinant derived HBcAg (RIA #2).

BRIEF DESCRIPTION OF THE DRAWINGS

FIG. 3. Southern blot analyses of the recombinant baculovirus VC2 DNA. Acc II digests of VC2 viral DNA were recovered from AcNPV, the recombinant virus VC2 and from the recombinant replicon pAcVC2. The DNA products were resolved by agarose gel electrophoresis and probed with either nick-translated coding regions of polyhedrin DNA (upper panel), or LCMV-N DNA (lower panel). A 5082 nucleotide fragment in the Acc II digest of VC2 DNA was identified by both DNA probes corresponding to the Acc II fragment present in the recombinant replicon pAcVC2. As expected, the polyhedrin probe identified a 2023 nucleotide Acc II fragment in wild-type AcNPV, whilst the LCMV-N probe did not hybridise to anv AcNPV DNA sequence.

FIG. 4. Northern blot analyses of total cellular RNA extracted from *S. frugiperda* cells infected with the recombinant virus VC2. The poly(A+) RNA species were recovered and processed as described in Methods. The blotted RNA was hybridised to nick-translated probes representing either the coding regions of the polyhedrin gene (left-hand panel), or the LCMV-N gene (right-hand panel). *S. frugiperda* cells infected with wild-type AcNPV, or the recombinant virus YM1.YN1 that expesses LCMV-N protein were processed similarly and utilised as positive hybridisation controls. The polyhedrin probe hybridised to a 1.2 kh mRNA species in cellular RNA obtained from VC2 infected cells which corresponded to the polyhedrin mRNA species present in AcNPV infected cells. The LCMV-N probe hybridised to a 2.25 kb mRNA species in cellular RNA obtained from VC2 infected cells which corresponded to the LCMV-N mRNA species present in the recomnbinant YM1.YN1 virus infected cells.

Open and filled triangles show nucleotide and amino acid differences, respectively, by comparison with sequences published by Ono and associates (1983).

Figure 1:
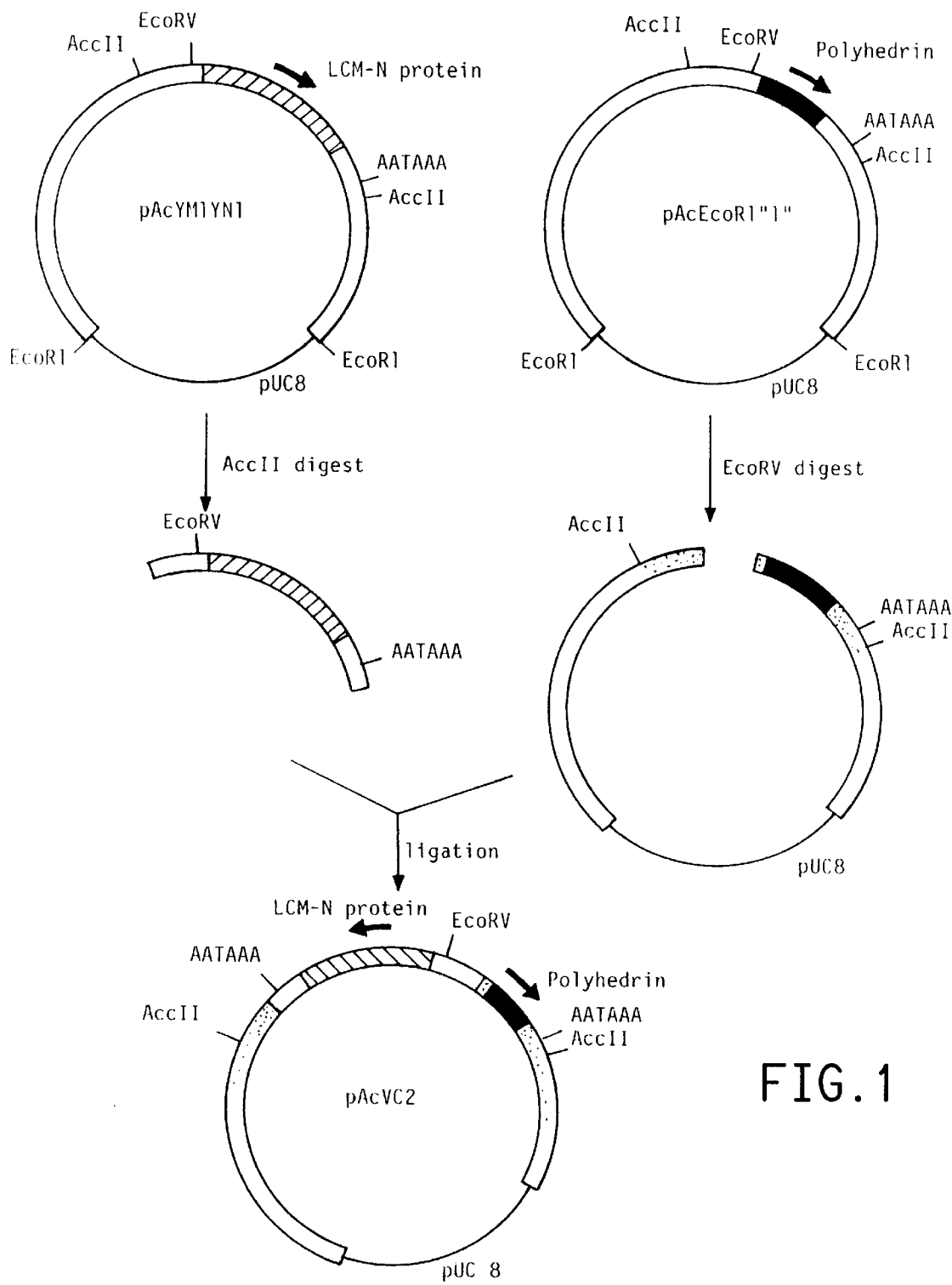
FIG. 1. Schematic of the construction of the plasmid replicon pAcVC2.
Figure 2A:
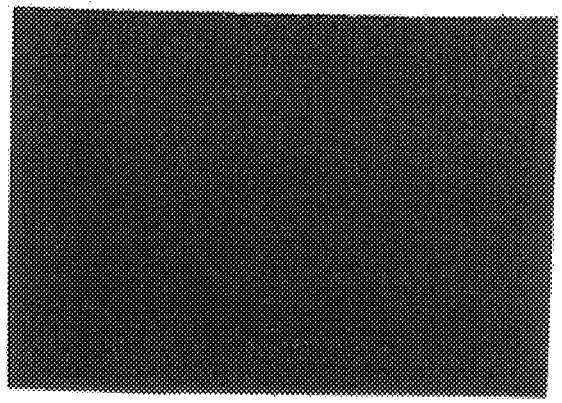
FIGS. 2A–G. Immunofluorescence of recombinant baculovirus-infected *S. frugiperda* cells. Cells were infected 36 h previously with AcNPV (a, b), or recombinant YM1.YN1 (Matsuura et al., 1987; c, d), or the recombinant virus VC2 derived from recombinant replicon pAcVC2 (e.g.). In panels a,c and e the cells Were fixed with acetone and examined for immunofluorescence using an LCMV-N specific monoclonal antibody (M. Buchmeir, Scripps Institute, La Jolla Calif., USA). To observe polyhedral occlusion bodies, the same cells were examined by light microscopy (b, d, g). Cells infected with AcNPV contained polyhedral inclusion bodies (b). Cells infected with recombinant YM1.YN1 virus did not (d). Cells inferted with recombinant VC2 showed both positive immunofluorescence (e) and polyhedral inclusion bodies (g). The hybrid ultraviolet/lighit micrograph of recombinant VC2 virus infected cells (f) clearly showed both immmunofluorescence and polyhedra.
Figure 2B:
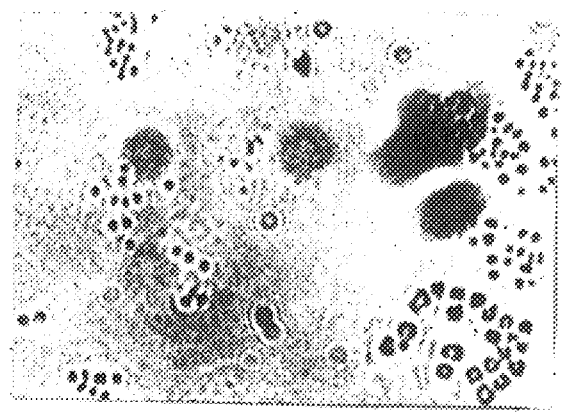
Figure 2C:
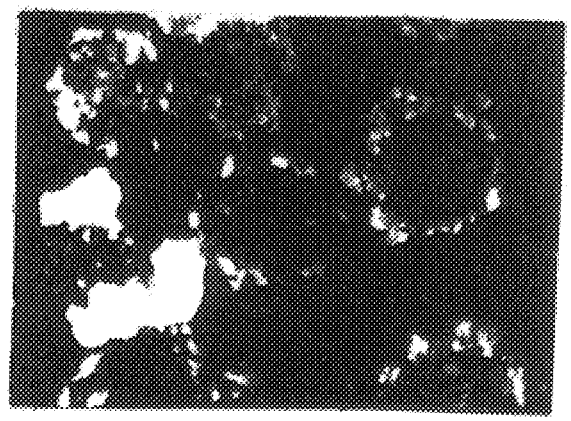
Figure 2D:
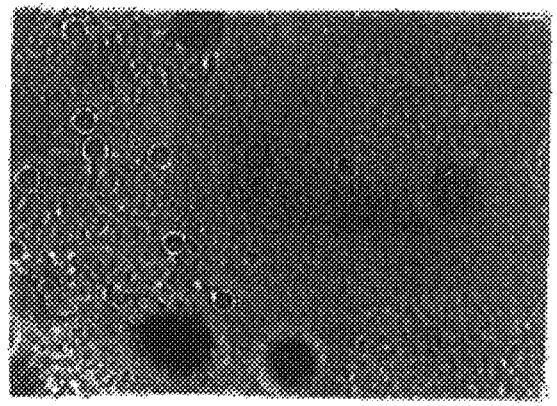
Figure 2E:
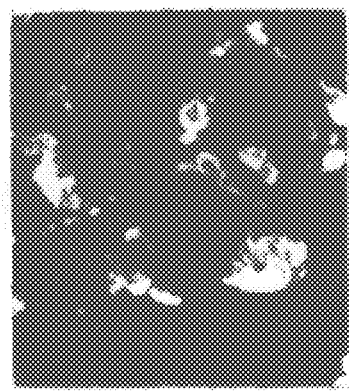
Figure 2F:
Figure 2G:
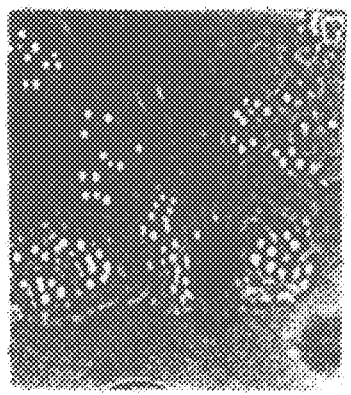
Figure 5:
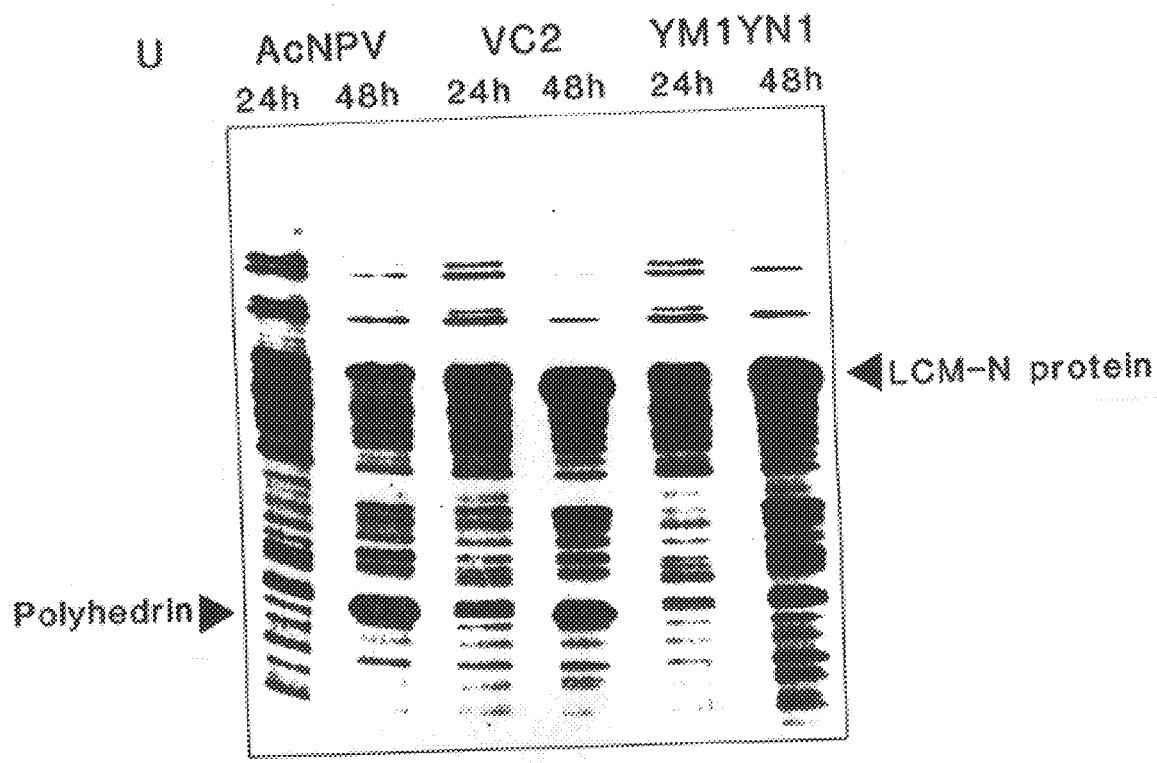
FIG. 5. Metabolic labelling of proteins produced during infection with the recombinant baculovirus VC2. *S. frugiperda* cells were infected with virus VC2, or with wild-type AcNPV, or recombinant virus YM1.YN1 (containing only the LCMV-N gene). Proteins were labelled at 24 h and 48 h post-infection for 1 hr with [$^{35}$S] Methionine, and the [$^{35}$S]-labelled proteins are resolved by gel electrophoresis and fluorographed. Uninfected cells were treated similarly (U). The positions of the LCMV-N and AcNPV polyhedrin proteins are indicated.
Figure 6:
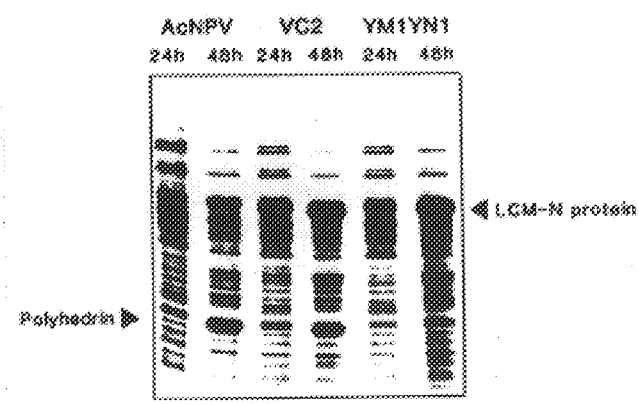
FIG. 6. Expression of the LCMV-N and polyhedrin protein by the recombinant baculovirus VC2. Details of infection are equivalent to those described in the legend to the FIG. 5 except that the protein gel was stained with Kenacid Blue. The positions of the LCMV-N and polyhedrin proteins are indicated.
Figure 7A:
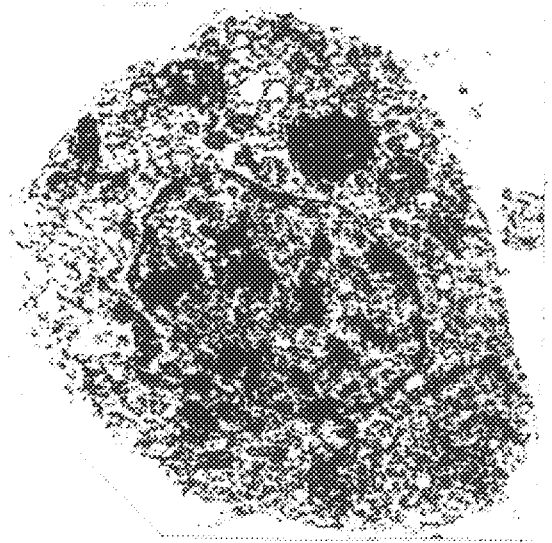
FIGS. 7A–E. Electron micrographs of uninfected or virus infected *S. frugiperda* cells. The panels show (a) uninfected *S. frugiperda*; (b) AcNPV infected *S. frugiperda*, illustrating polyhedral inclusion bodies in the nucleus; (c) *S. frugiperda* infected with recombinant virus YM1.YN1, note the dense cytoplasmic LCMV-N protein inclusion bodies; (d) and (e) *S. frugiperda* cells infected with recombinant virus VC2 exhibiting both intranuclear polyhedral inclusion bodies and cytoplasmic LCMV-N protein inclusion bodies.
Figure 7B:
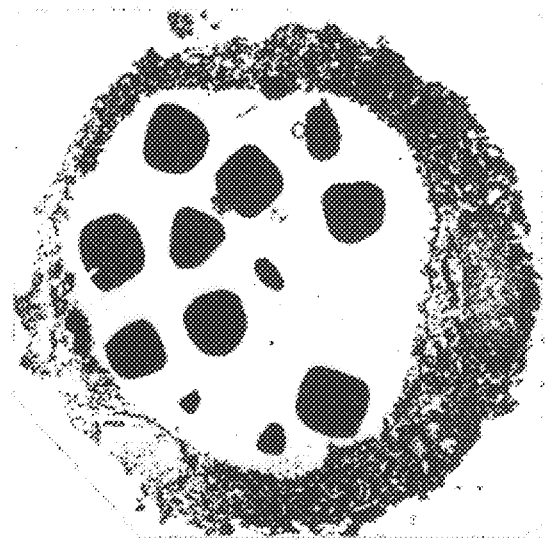
Figure 7C:
Figure 7D:
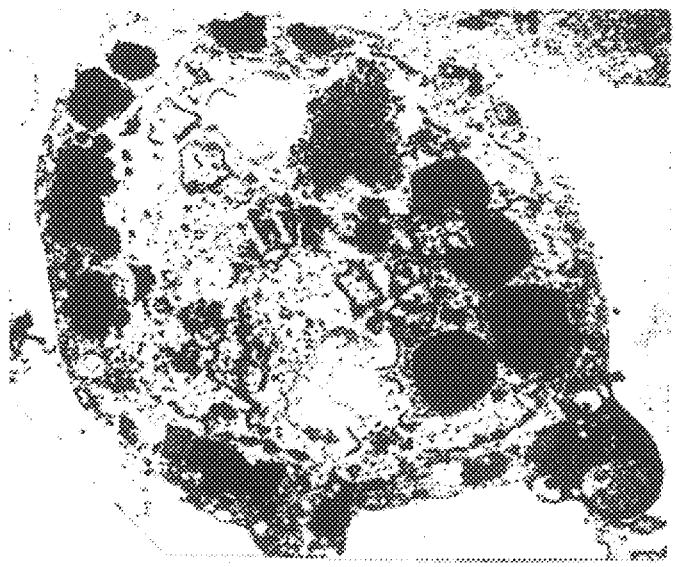
Figure 7E:
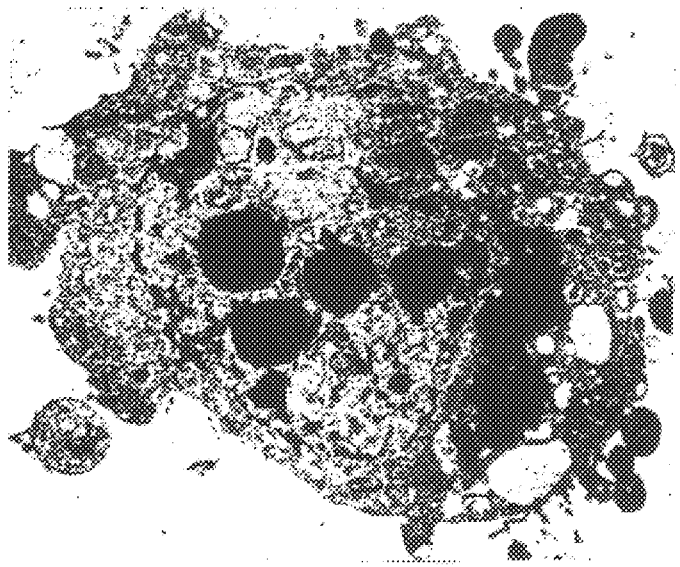
Figure 8:
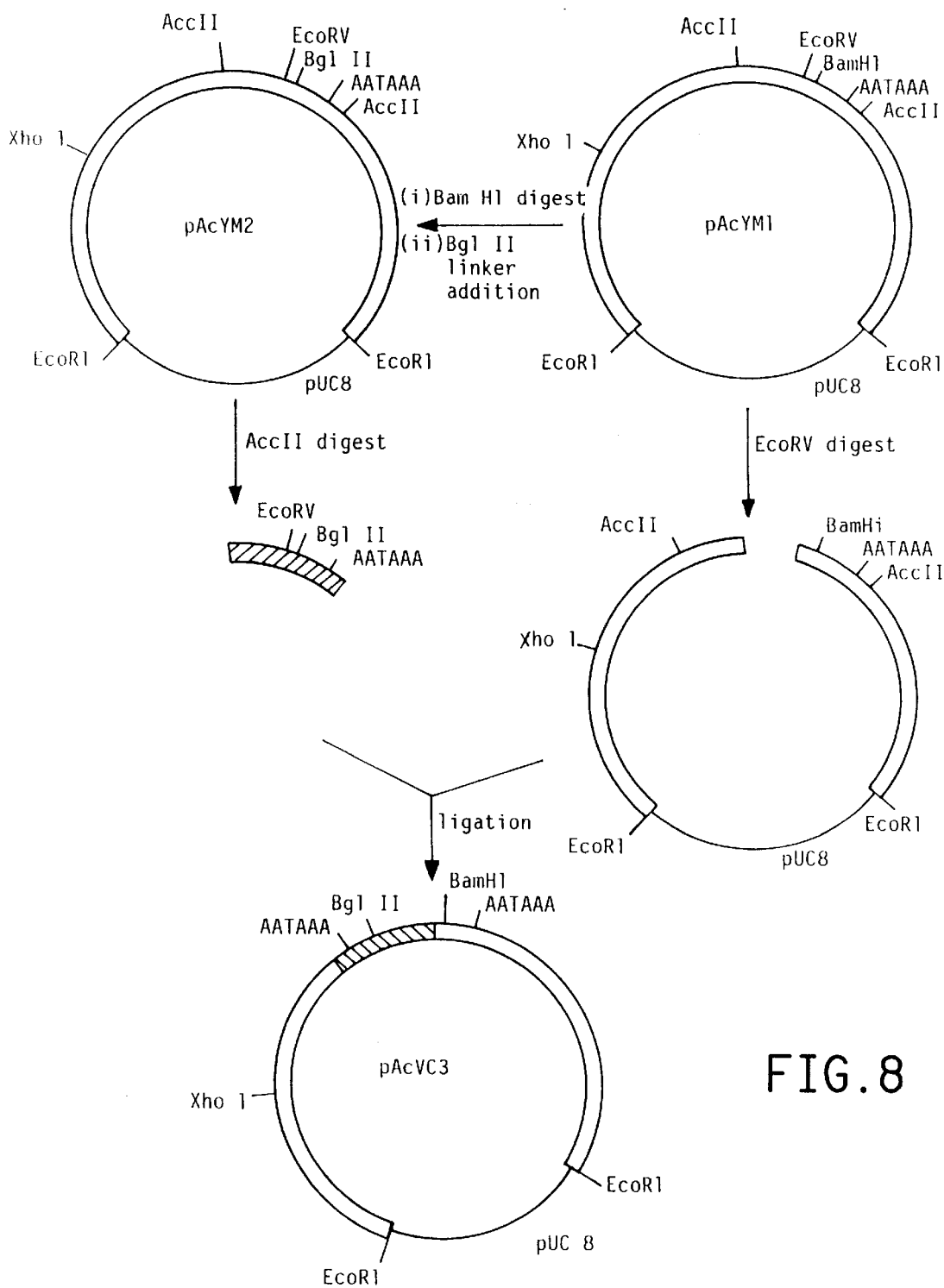
FIG. 8. Schematic of the construction of the plasmid replicon pAcVC3.
Figure 9:
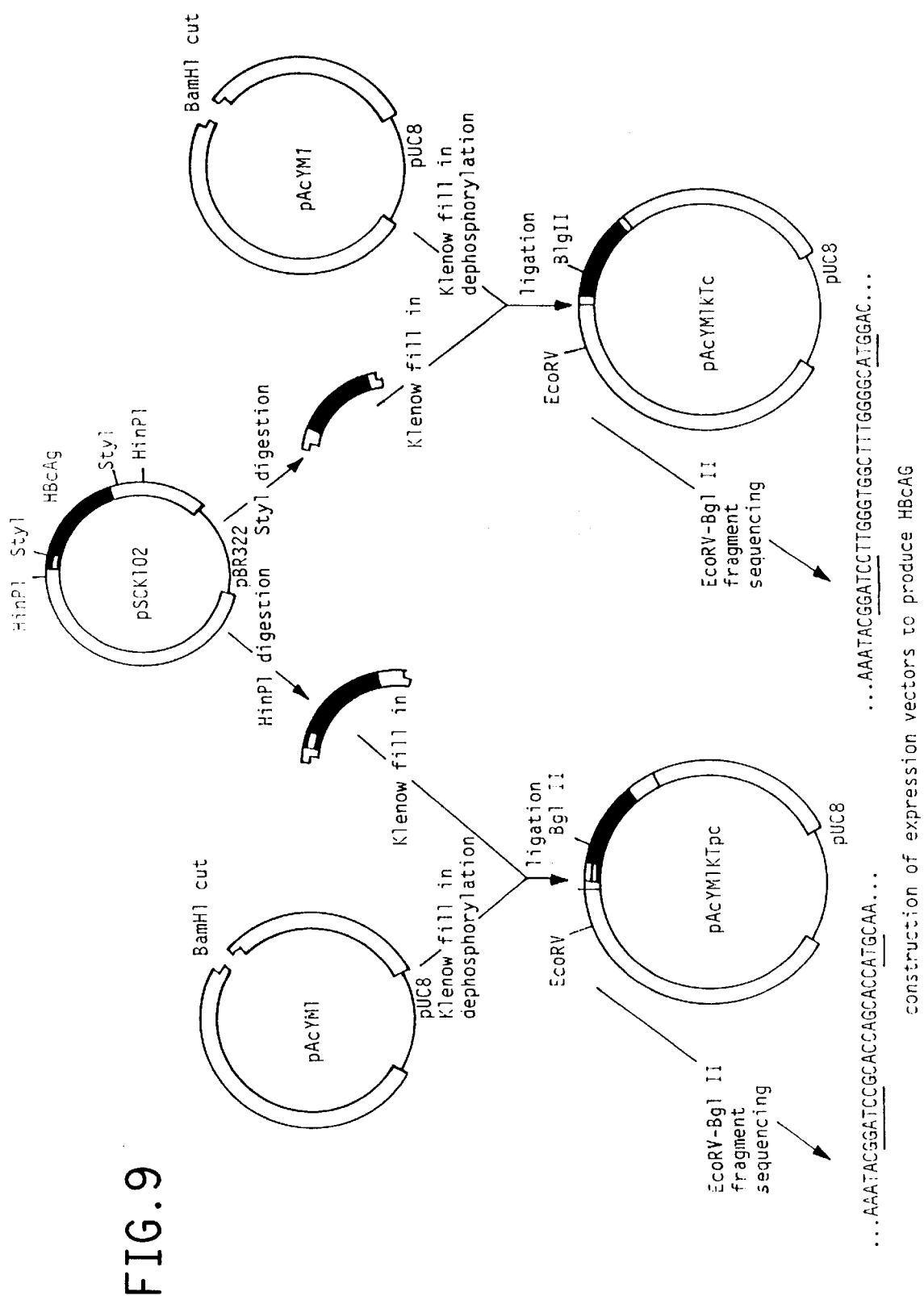
FIG. 9. Schematic diagram of the construction of the transfer vectors pAcYM1KTpc and pAcYM1KTc as described in Methods. In the sequences shown at the sites of insertion the BamHI site and the initiation codons of the HBpcAg and HBcAg are underlined.
Figure 10:
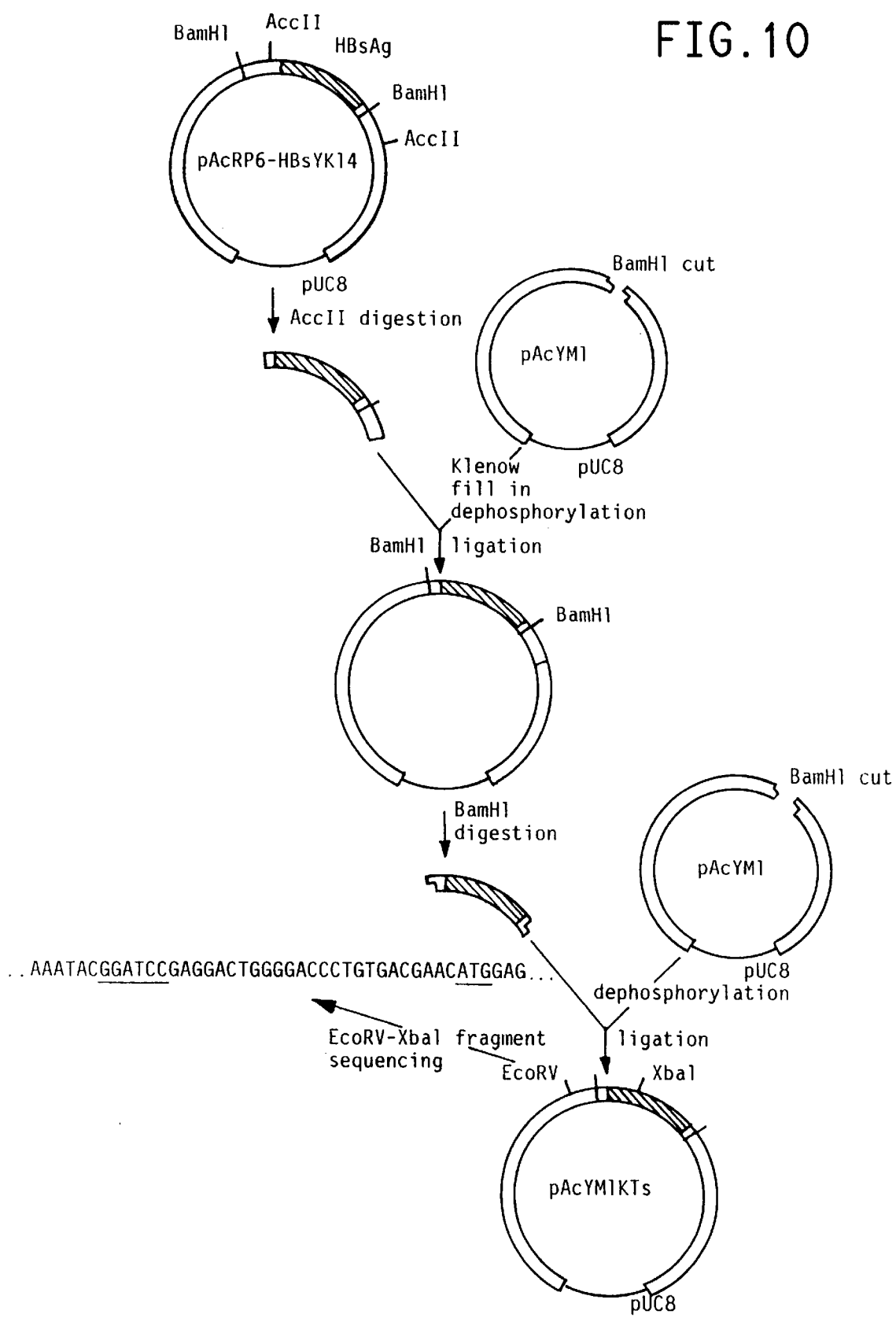
FIG. 10. Schematic diagram of the construction of the transfer vector pAcYM1KTs as described in Methods. In the sequence shown the BamHI site and the initiation codon of the HBsAg are underlined.
Figure 11:
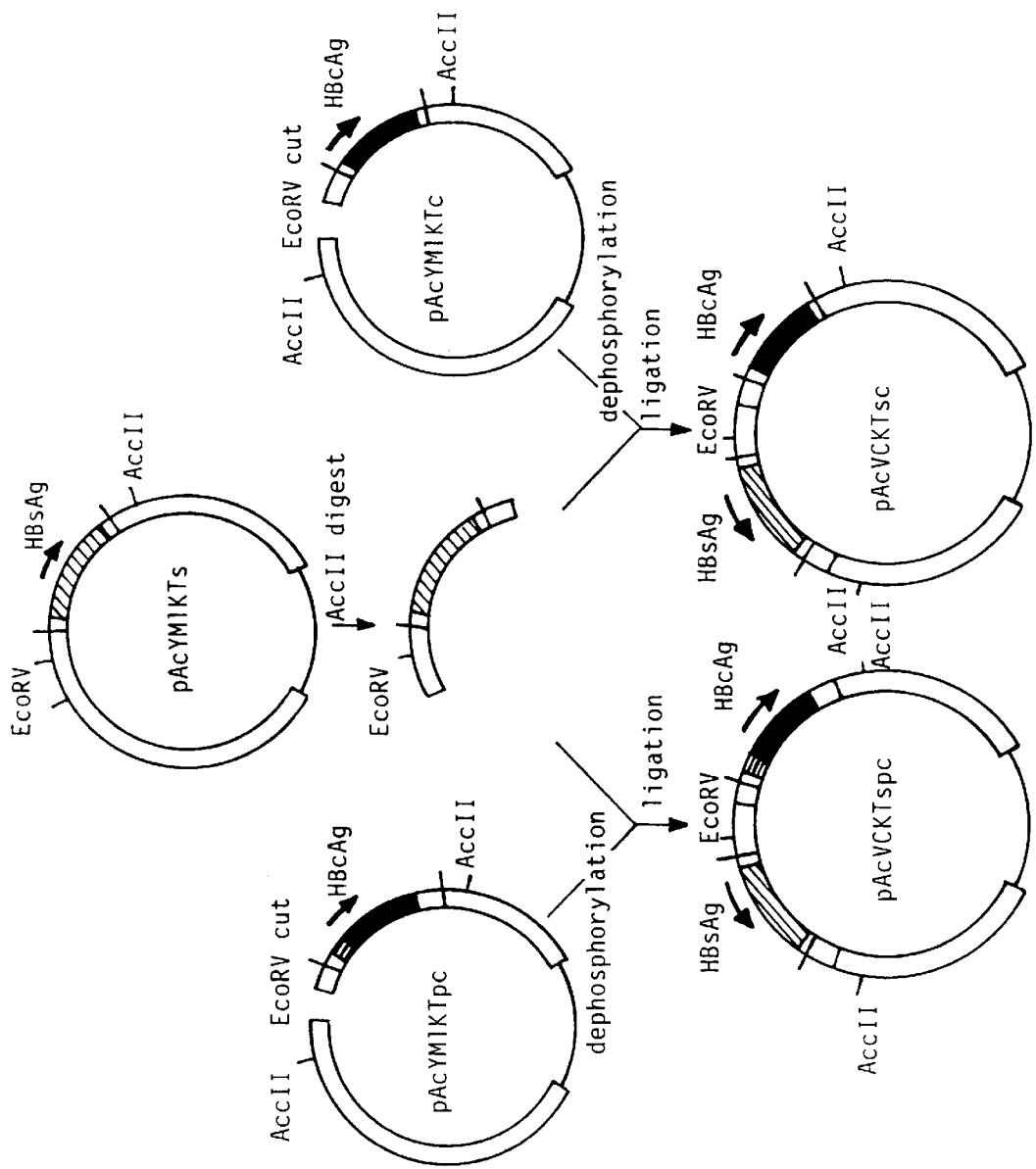
FIG. 11. Schematic diagram of the construction of the transfer vectors pAcVCKTspc and pAcVCKTsc as described in Methods.
Figure 12:
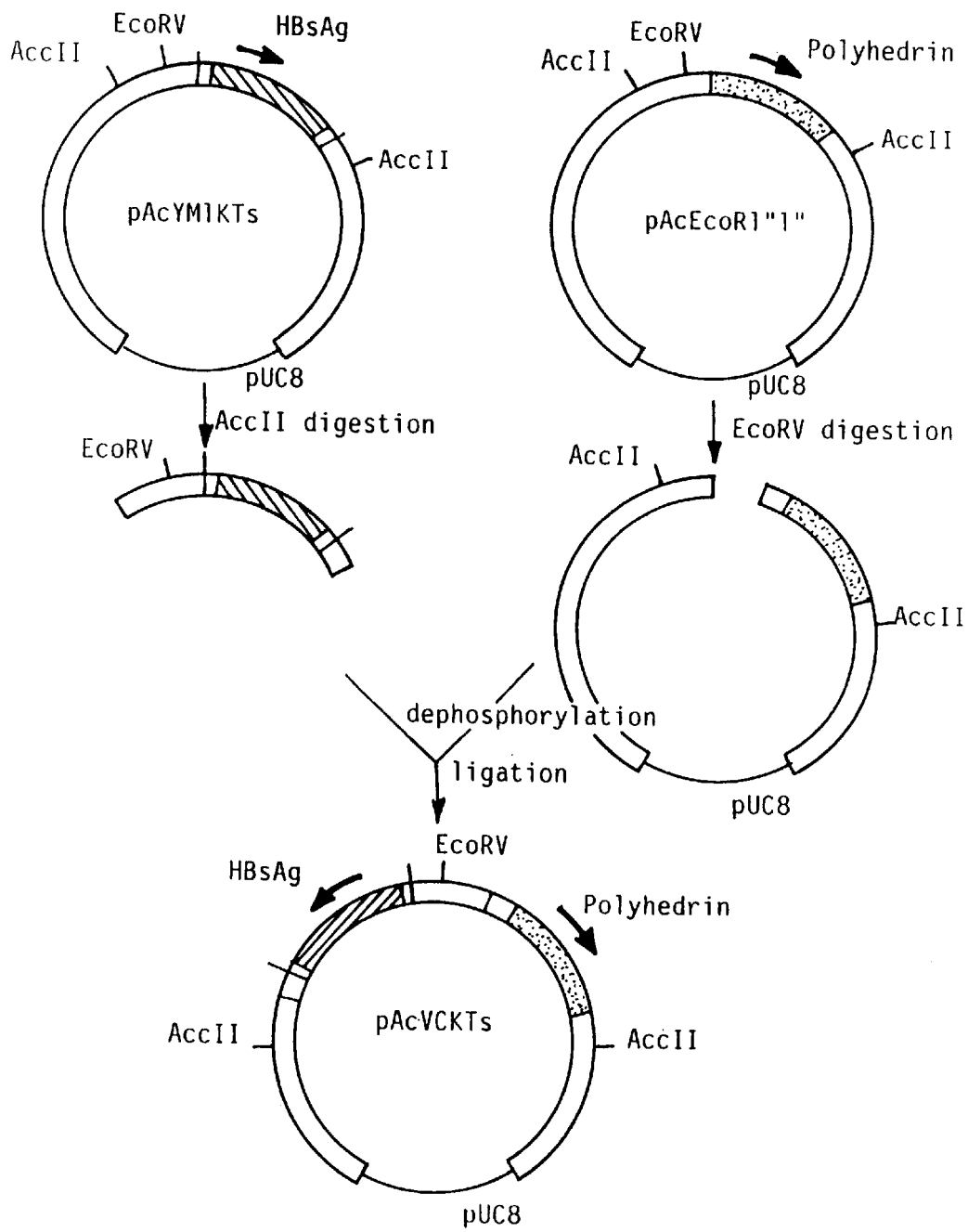
FIG. 12. Schematic diagram of the construction of the transfer vector pAcVCKTs as described in Methods.
Figure 13:
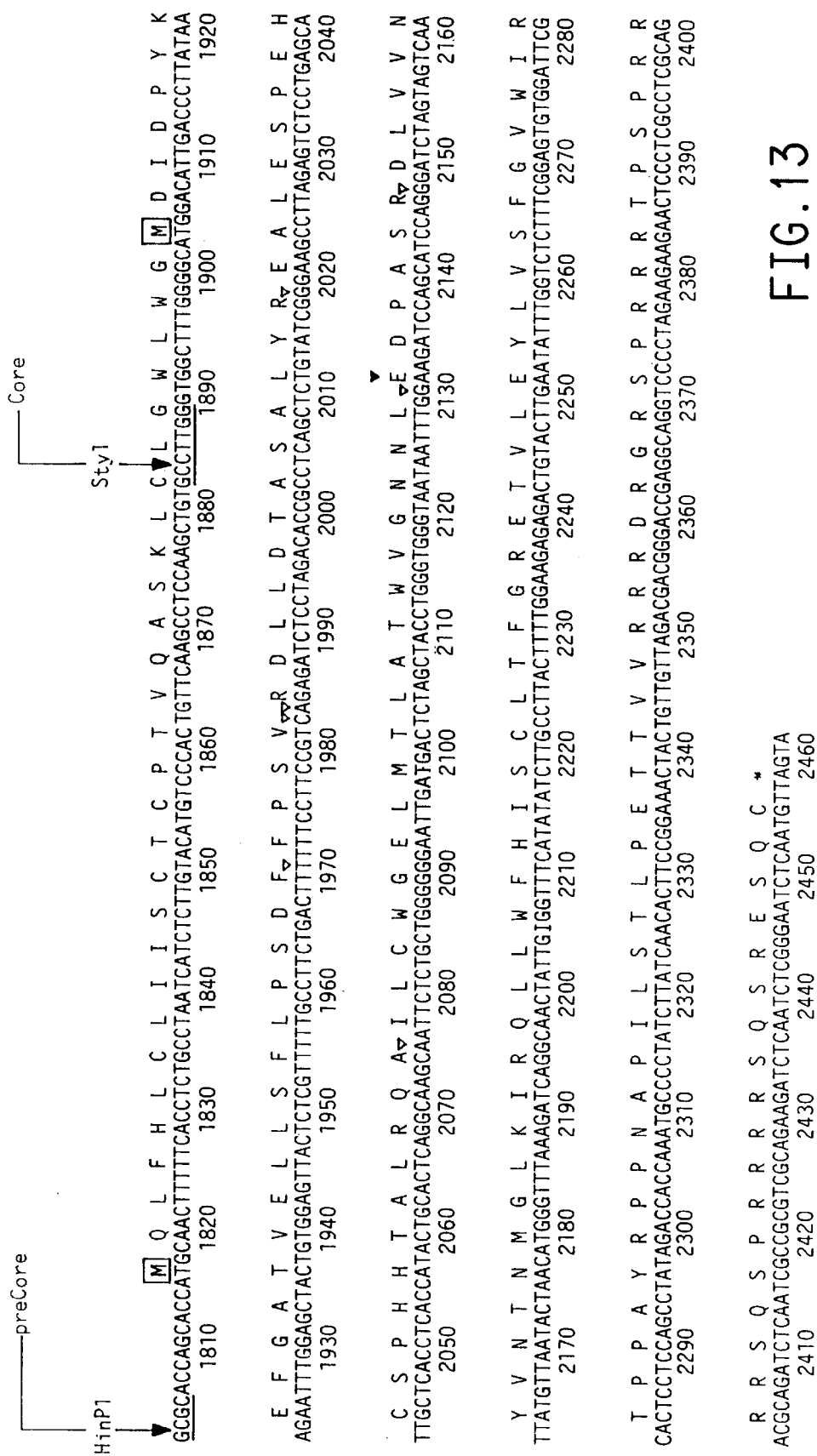
FIG. 13. The sequences of the HBcAg and HBpcAg genes and amino acids. The methionine codons are boxed that initiate the preC and C gene products.
Figure 14A:
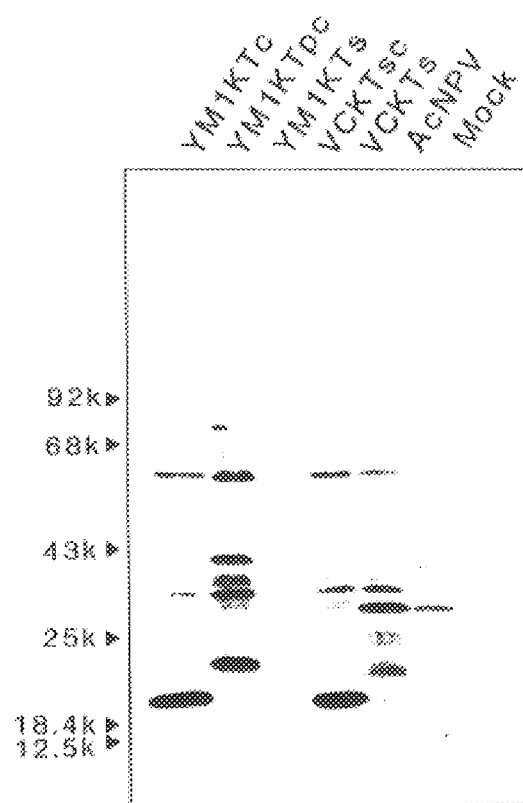
Figure 14B:
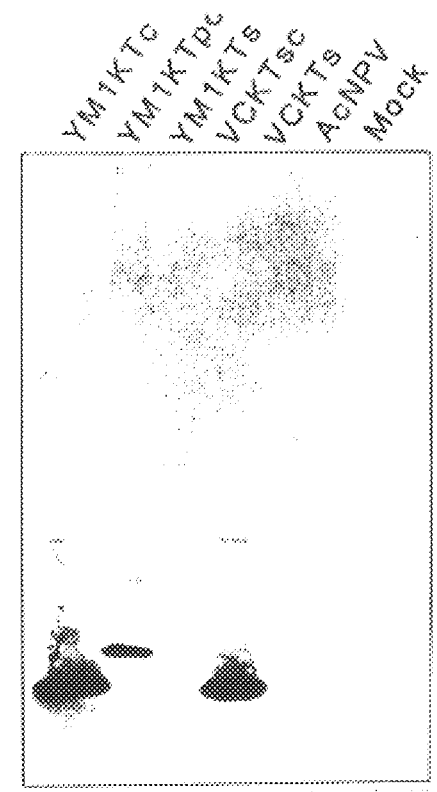

FIG. 14. Metabolic labelling (left) and Western blot analysis (right) of proteins expressed by recombinant baculoviruses. *S. frugiperda* cells were infected with recombinant viruses or wild-type AcNPV. Proteins were labelled at 48 h post-infection for 3 h with [$^{35}$S] methionine and the $^{35}$S-labelled proteins recovered, resolved by gel electrophoresis, blotted to nitrocellulose membranes and fluorographed (left), or detected immunologically with anti-HBcAg serum (right). Uninfected cells were treated similarly (Mock). The positions of HBcAg (C), HBpcAg (pC), HBsAg (S), and AcNPV polyhedrin protein (P) are indicated. The positions of molecular weight marker proteins (12.5–92 kiloDaltons) are indicated on the left.

Figure 15A:
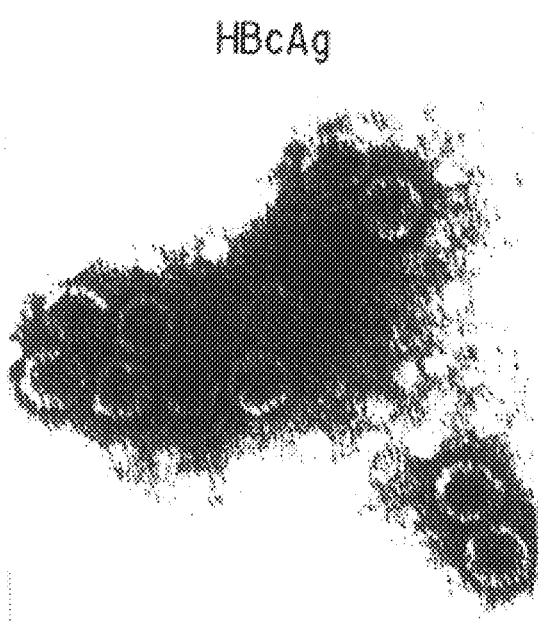
Figure 15B:
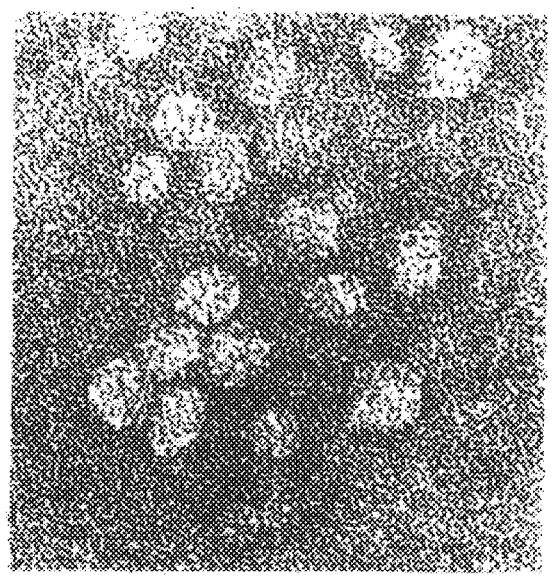

FIG. 15A and B. Electron micrographs of HBcAg and HBsAg particles produced by *S. frugiperda* cells infected with recombinant viruses. (A) HBcAg was extracted by sonication from YM1KTc virus infected cells (alternatively. on occasion, by freeze-thawing the cells) and purified by CsCl isopicnic centrifugation as described in Methods, then stained with 1% uranyl acetate. (B) HBsAg was collected from the supernatant fluids of YM1KTs virus infected cells, clarified by centrifugated (2,000×g) after treatment with 7% PEG, the antigen pelleted after adjusting the supernatant fluids with 9% PEG and stained with 1% uranyl acetate.

Figure 16B:
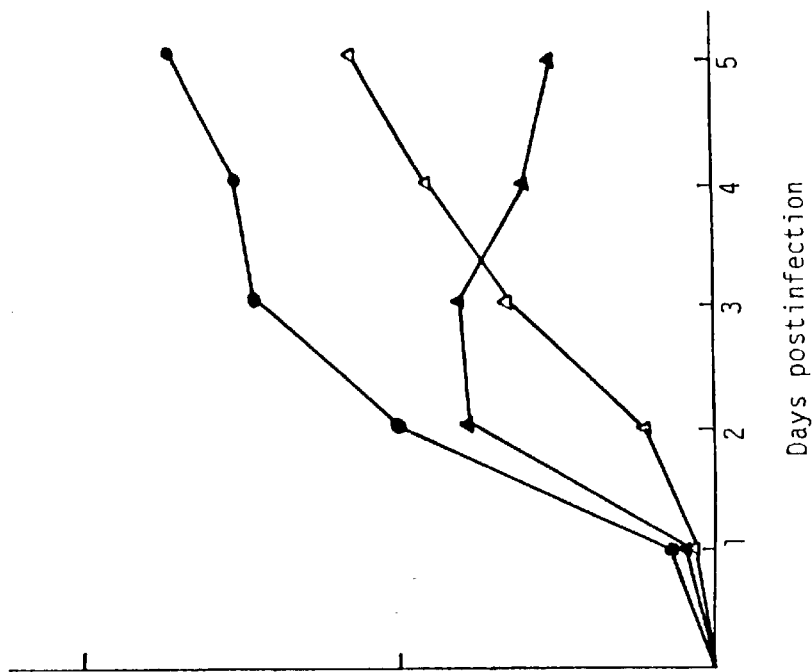
Figure 16A:
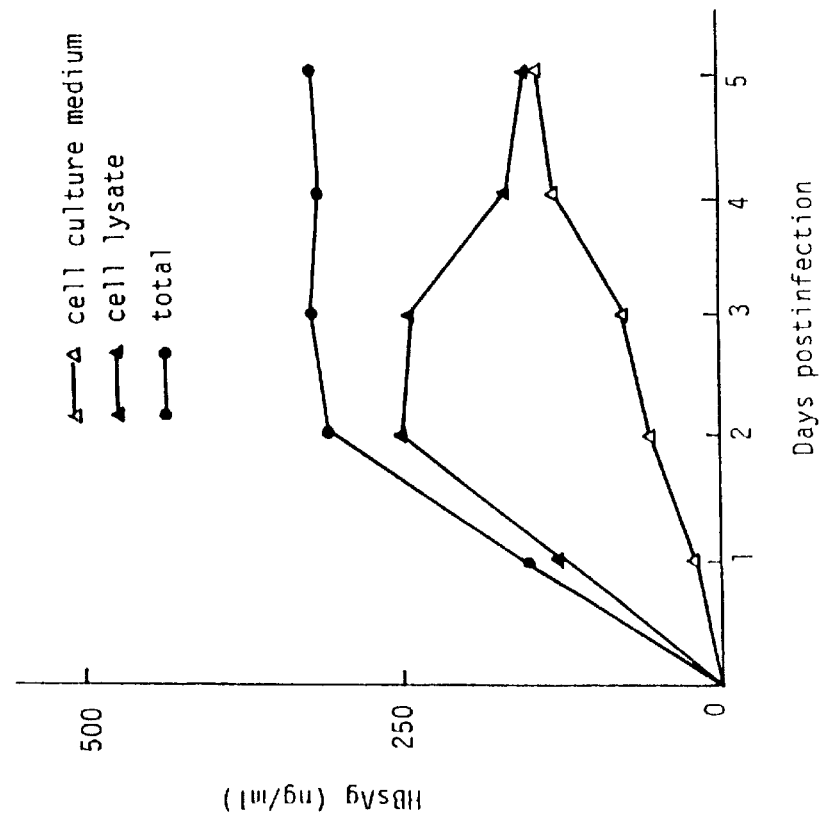

FIG. 16A and B. Kinetics of HBsAg synthesis from *S. frugiperda* cells infected with the recombinant YM1KTs (A) or VCKTsc (B). Infected cells (5×10$^8$) were cultured in 500 ml media with stirring. Samples (5 ml) were collected every day and the media and cells separated by low speed centrifugation. Cells were lysed by sonication after gently rinsing with PBS. Viral HBsAg in the cell lysates, or in the clarified culture medium were measured by solid-phase RIA (AUSTRIA II, Abbott Laboratories) with the human derived HBsAg as a positive control and to quantitate the yields (see Methods). The data are expressed as the antigen per ml of original medium.

Figure 17:
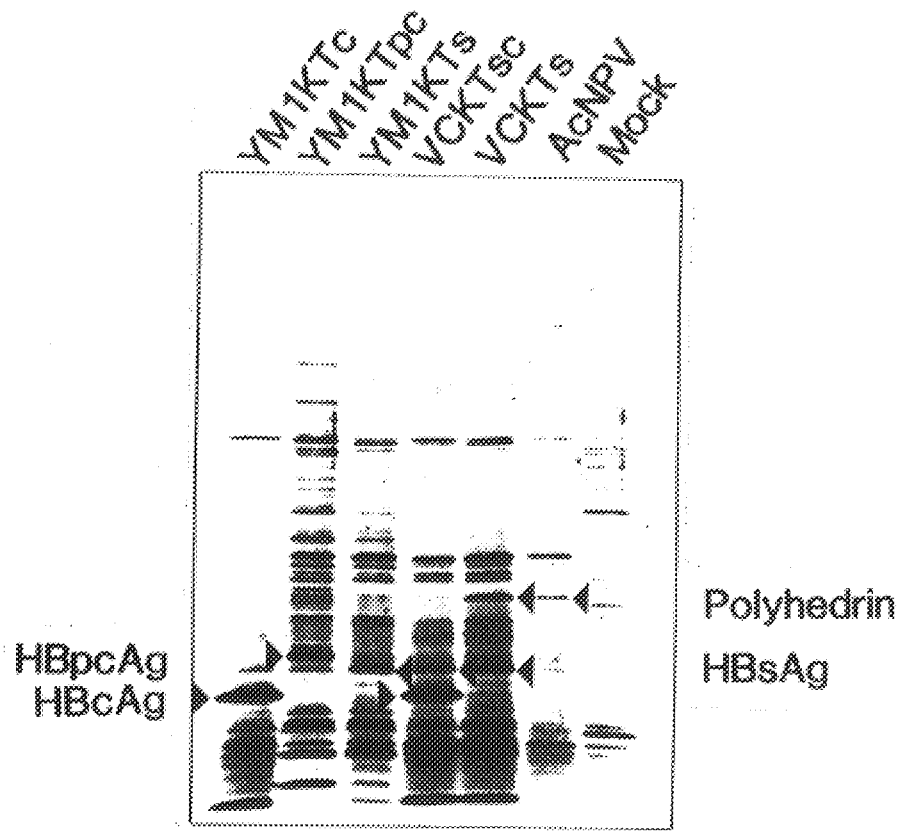

FIG. 17. Expression of HBcAg, HBpcAg, HBsAg and polyhedrin protein by recombinant baculoviruses. Cell extracts from recombinant or AcNPV infected cells were obtained at 2 days post-infection. After resolution by SDS-PAGE, the gel was stained with Kenacid Blue. The positions of the HBpcAg, HBcAg, HBsAg and polyhedrin protein are indicated.

Figure 18A:
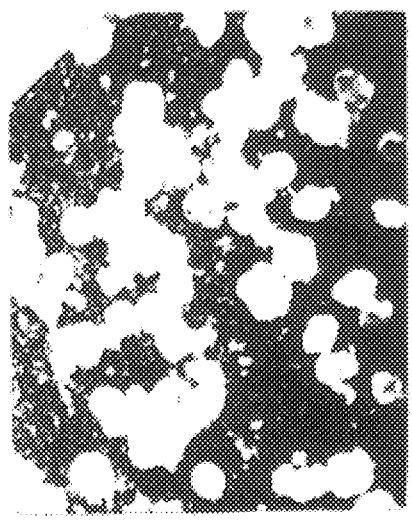
Figure 18B:
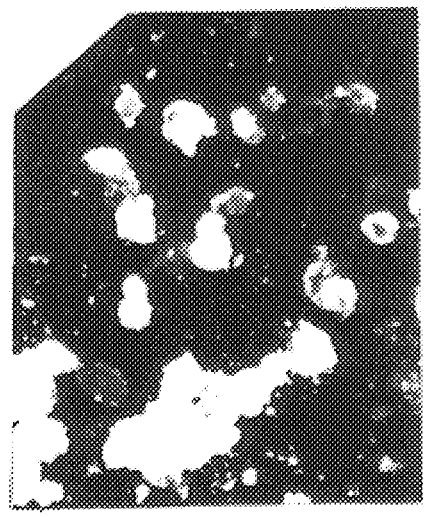
Figure 18C:
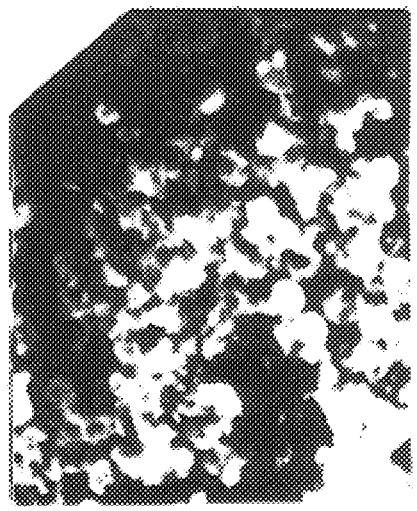

FIG. 18. Immunofluorescence of recombinant baculovirus-infected *S. frugiperda* cells. *S. frugiperda* cells infected 72 h previously with a recombinant baculovirus named VCKTsc were fixed with acetone and examine, by indirect immunofluorescent assay as described in Methods, using (A) human anti-HBc serum, or (B) mouse monoclonal anti-HBs ascitic fluids. Uninfected *S. frugiperda* cells were treated similarly and examined using mouse monoclonal anti-HBs (C).

Figure 19A:
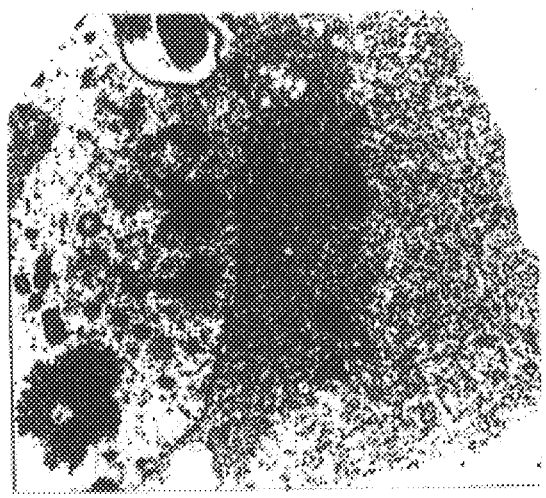
Figure 19B:
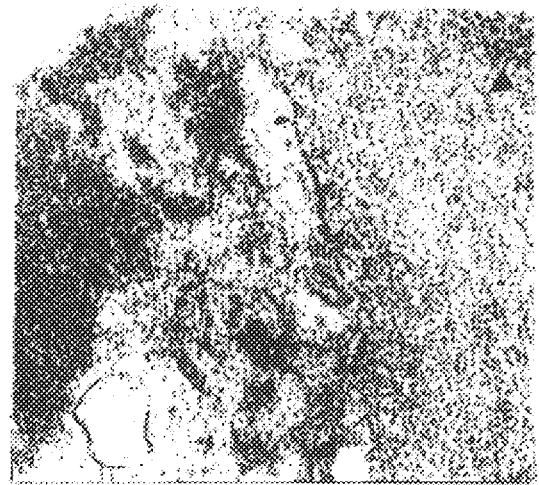

FIG. 19 Eletron micrographs of virus infected *S. frugiperda* cells. In (A), a thin section of a cell infected with recombinant VCKTsc is shown. In (B), another cell is shown at a higher magnification. The filled triangles point to the massed positions of HBcAg.

Figure 20A:
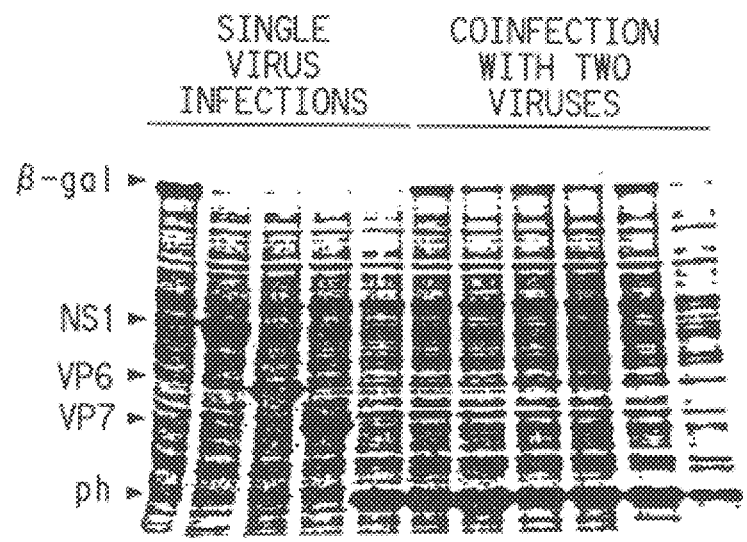
Figure 20B:
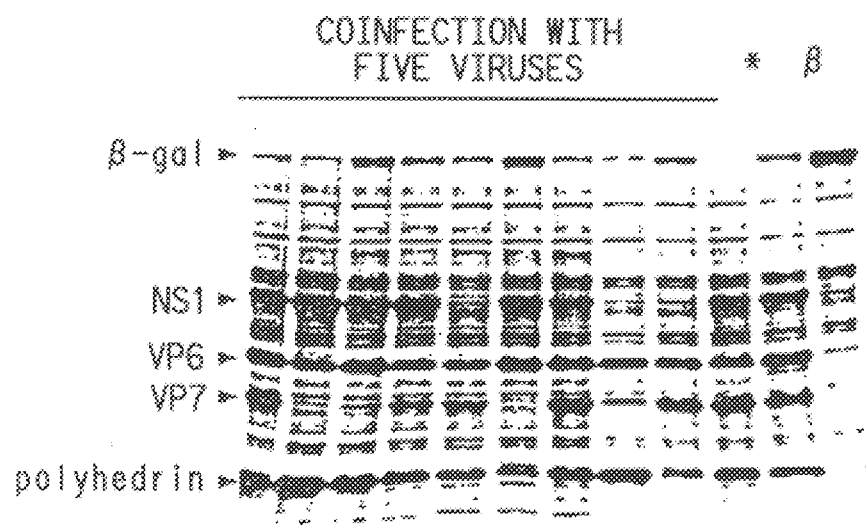

FIGS. 20A and B. Analysis of the protein synthesis in single or multiple virus infections.

Panel A: Single virus infections and coinfection with two viruses. The recombinant viruses, each expressing a single foreign gene either β-galactosidase(β-gal), or bluetongue virus NS1, or VP6, or VP7, and wild type AcNPV to express polyhedrin were used to infected Sf cells as indicated. For the co-infection AcNPV and the recombinant that synthesizes β-galactosidase were employed.

Panel B: Co-infection with five viruses. Sf cells were coinfected at a multiplicity of 5 FPU per cell with recombinant baculoviruses each expressing a single gene as well as AcNPV, the infected cells were diluted, mixed with uninfected cells to form monolayers, covered with agar and incubated at 28° C. for 3 days. Individual plaques (infectious centers) were picked and monolayers of Sf cells were infected with the viruses recovered from such plaques. Cells were harvested at 3 days post-infection, washed with phosphate-buffered saline, and lysed at 4° C. in 50 mM Tris hydrochloride (pH 8), 150 mM NaCl-0.5% Nonidet P-40. Protein dissociation buffer (10% β-mercaptoethanol, 10% sodium dodecyl sulfate [SDS], 25% glycerol, 10 mM Tris hydrocloride [pH 6.8], 0.02% bromphenol blue) was added to the samples, and the mixtures were incubated at 100° C. for 5 min. Proteins were separated by SDS-PAGE and stained with Coomassie brilliant blue. As controls, the expression from uncloned cells under the same condition is shown for either the five virus co-infection (*), or an infection with only the lacZ recombinant virus (β).

Figure 21A:
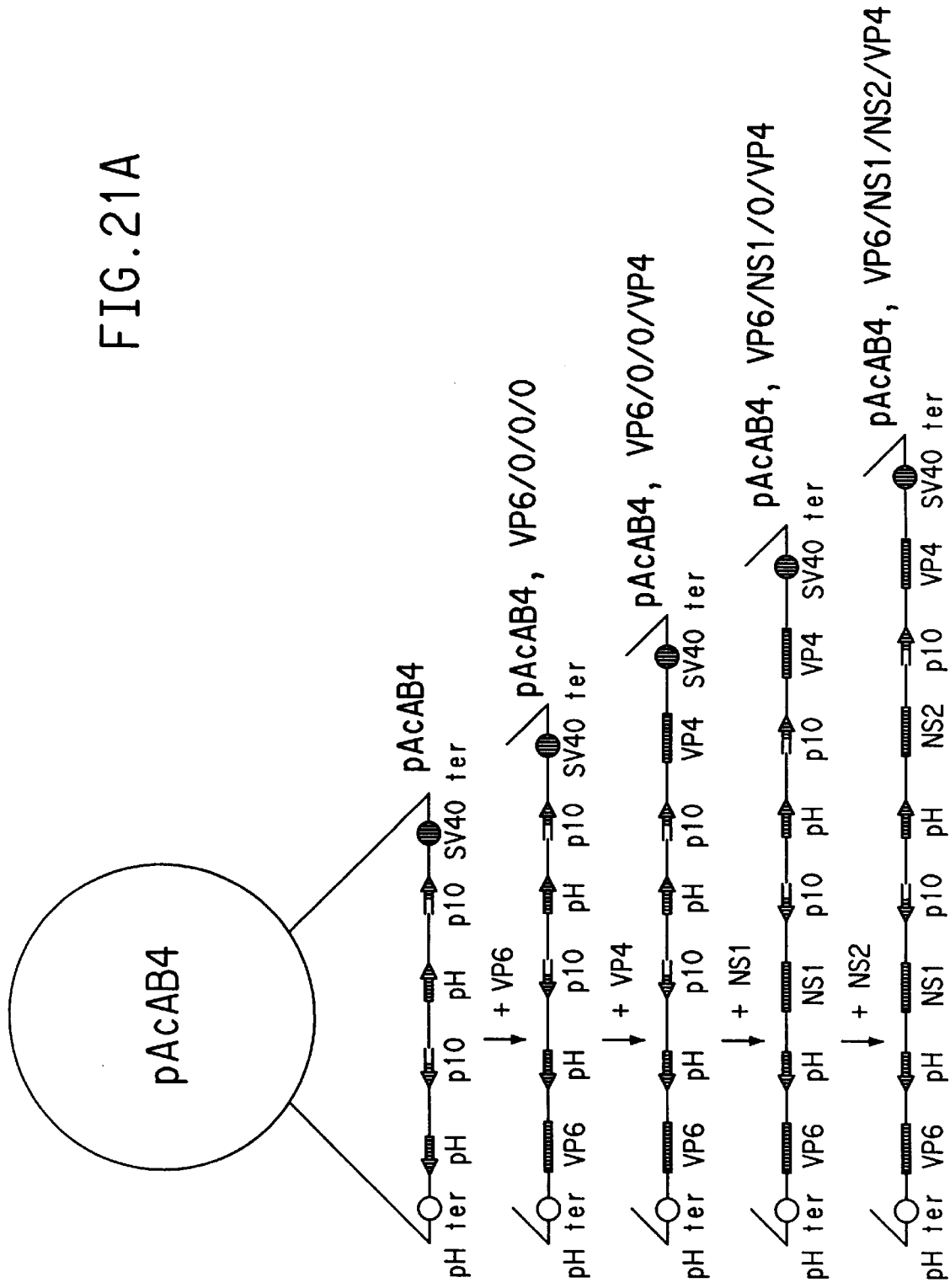
Figure 21B:
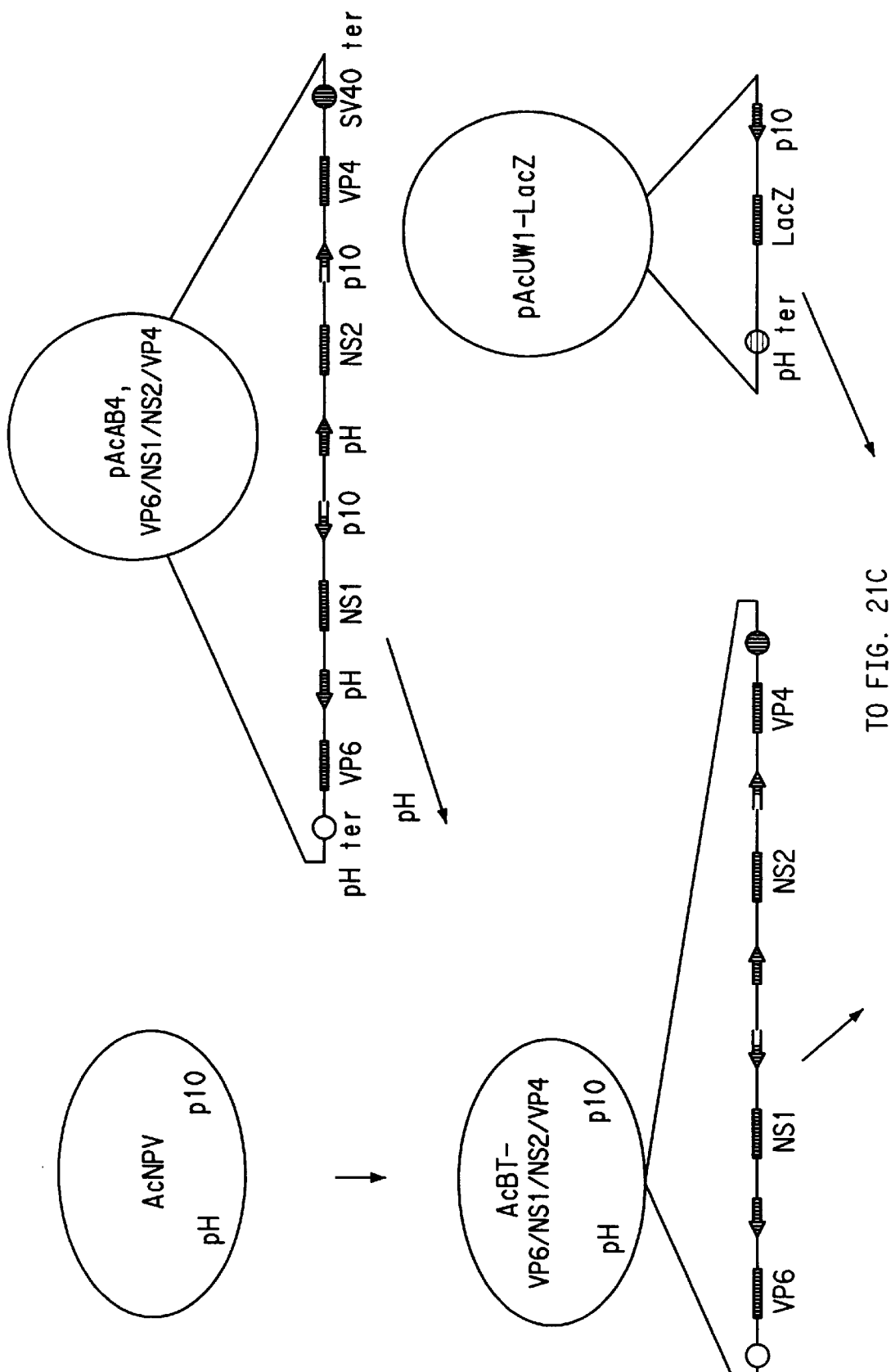
Figure 21C:
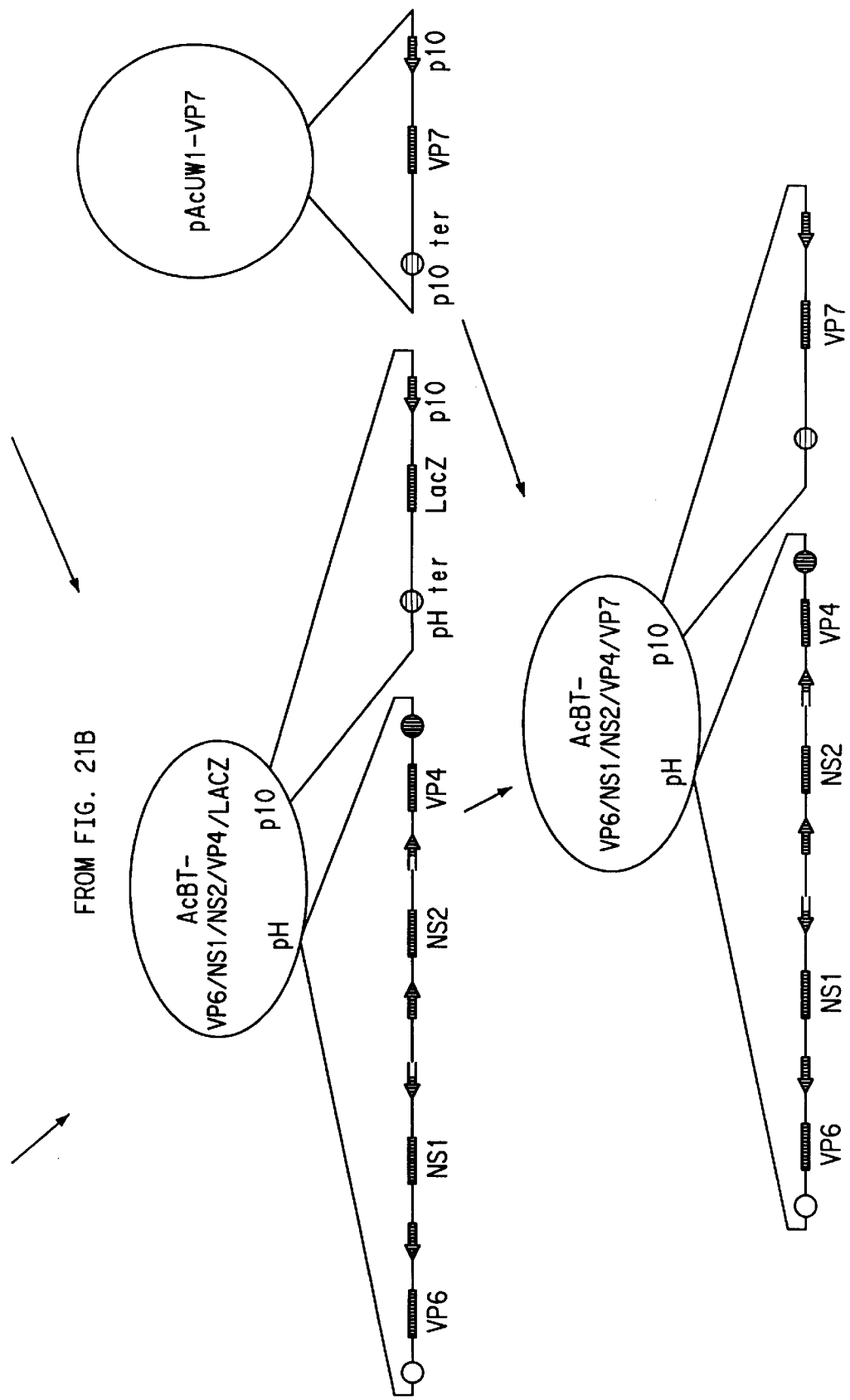

FIGS. 21A and B. Schematic diagram showing the sequential steps utilized for generating the quintuple recombinant baculovirus.

Figure 22:
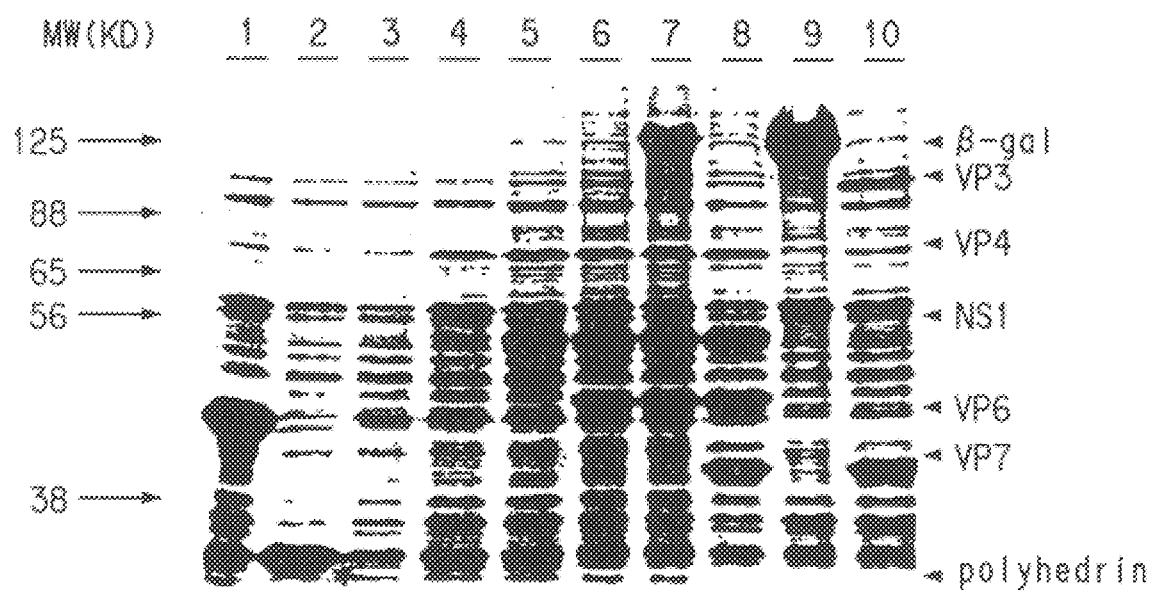

FIG. 22. Synthesis of foreign proteins by quintuple recombinant baculoviruses. Sf cells were infected at a multiplicity 5 PFU per cell with the recombinant baculoviruses, or with wild-type AcNPV. Cells were harvested at 3 days post-infection. Proteins were separated by 10% SDS-PAGE and stained with Coomassie brilliant blue.

Lane 1—Single recombinant baculovirus synthesizing bluetongue virus VP6 (Roy et al., 1990);

Lane 2—Wild type AcNPV, polyhedrin band indicated by asterisk;

Lanes 3–5—Recombinant baculoviruses generated with the intermediate transfer vector constructs pAcAB4.VP6/0/0/0, pAcAB4.VP6/0/0/VP4 and pAcAB4.VP6/NS1/0/VP4, respectively;

Lane 6—Quadruple recombinant baculovirus AcBT-VP6/NS1/NS2/VP4; Lane 7—quintuple recombinant baculovirus AcBT-VP6/NS1/NS2/VP4/lacZ;

Lane 8—Quintuple recombinant baculovirus AcBTVP6/NS1/NS2/VP4/VP7;

Lane 9—Recombinant baculovirus BacPAK6 (Kitts and Possee, 1993);

Lane 10—Dual recombinant baculovirus synthesizing VP3 and VP7 (French and Roy, 1990).

REFERENCES

Ahn, B.-Y., Rosel, J., Cole, N. B. and Moss, B.: Identification and expression of rpo19, a vaccinia virus gene encoding a 19-kilodalton DNA-dependent RNA polymerase subunit. J. Virol. 66 (1992) 971–982.

Belyaev, A. S. and Roy, P.: Development of baculovirus triple and quadruple expression vectors: co-expression of three or four bluetongue virus proteins and the synthesis of bluetongue virus-like particles in insect cells. Nucleic Acids Research 21 (1993) 1219–1223.

Cussac, V., Ferrero, R. L. and Labigne, A.: Expression of Helicobacter pylori urease genes in *Escherichia coli* grown under nitrogen-limiting conditions. J. Bacteriol. 174 (1992) 2466–2473.

French, T. J. and Roy, P.: Synthesis of bluetongue virus core-like particles by a recombinant baculovirus expressing the two major structural core proteins of bluetongue virus. J. Virol. 64 (1990) 1530–1536.

French, T. J., Marshall, J., and Roy, P.: Assembly of double-shelled, virus like particles of bluetongue virus by the simultaneous expression of four structural proteins. J. Virol. 64 (1990) 5695–5700.

Janeway, C. A., Jr.: The T cell receptor as a multicomponent signalling machine. Annu. Rev. Immunol. 10 (1992) 645–674.

Kitts, P. A. and Possee, R. D.: A method for producing recombinant baculovirus expression vectors at high frequency. BioTechniques 14 (1993) 810–817.

Le Blois, H., French, T., Mertens, P. P., Burroughs, J. N. and Roy, P.: The expressed VP4 protein of bluetongue virus binds GTP and is the candidate guanylyl transferase of the virus. Virology 189 (1992) 757–761.

Malpartida F. and Hopwood, D. A.: Molecular cloning of the whole biosynthetic pathway of a Streptomyces antibiotic and its expression in a heterologous host. Nature 309 (1984) 462–464.

Maniatis, T., Fritsch, E. F. and Sambrook, J.: Molecular cloning: a laboratory manual. Cold Spring Harbor Laboratory Press, Cold Spring Harbor, N.Y., 1982.

Oldfield, S., Adachi, A., Urakawa, T., Hirasawa, T. and Roy, P.: Purification and characterization of the major group-specific core antigen VP7 of bluetongue virus synthesized by recombinant baculovirus. J. Gen. Virol. 71 (1990) 2649–2656.

Possee, R. D.: Cell surface expression of influenza virus haemagglutinin in insect cells using a baculovirus vector. Virus Res. 5 (1986) 43–59.

Possee, R. D. and Howard, S C.: Analysis of the polyhedrin gene promoter of the *Autographa californica* nuclear polyhedrosis virus. Nucleic Acids Res. 15 (1987) 10233–10248.

Roy, P. and Gorman, B. M.: In Roy, P. and Gorman, B. M. (eds) Bluetongue Viruses—Current Topics in Microbiology and Immunology. Springer-Verlag, Heidelberg (1990) pp. 1–200.

Roy, P., Adachi, A., Urakawa, T., Booth, T. F. and Thomas, C. P.: Identification of bluetongue virus VP6 protein as a nucleic acid-binding protein and the localization of VP6 in virus-infected vertebrate cells. J. Virol. 64 (1990) 1–8.

Thomas, C. P., Booth, T. F. and Roy, P.: Synthesis of bluetongue virus-encoded phosphoprotein and formation of inclusion bodies by recombinant baculovirus in insect cells: it binds the single-stranded RNA species. J. Gen. Virol. 71 (1990) 2073–2083.

Urakawa, T. and Roy, P.: Bluetongue virus tubules made in insect cells by recombinant baculoviruses: expression of the NS1 gene of Bluetongue virus serotype 10. J. Virol. 62 (1988) 3919–3927.

Weyer, U., Knight, S. and Possee, R. D.: Analysis of very late gene expression by *Autographa californica* nuclear polyhedrosis virus and the further development of multiple expression vectors. J. Gen. Virol. 71 (1990) 1525–1534.

Weyer, U. and Possee, R. D.: A baculovirus dual expression vector derived from the *Autographa californica* nuclear polyhedrosis virus polyhedrin and p10 promoters: co-expression of two influenza virus genes in insect cells. J. Gen. Virol. 72 (1991) 2967–2974.

Woychik, N. A. and Young, R. A.: RNA polymerase II: subunit structure and function. Trends Biochem. Sci. 15 (1990) 347–351.

What is claimed is:

1. A plasmid replicon for use in introducing a plurality of genes into an expression vector, said plasmid replicon comprising double-stranded DNA containing the following sequences:

(a) a first sequence allowing the replicon to be reproduced in a bacterial host;

(b) a second sequence adapted to permit an intervening sequence located between said second sequence and a third sequence of (c) to be introduced into an expression vector;

(c) a third sequence adapted to permit an intervening sequence located between said second sequence of (b) and said third sequence to be introduced into an expression vector; and (d) a fourth sequence which is an intervening sequence located between said second sequence of (b) and said third sequence of (c), wherein said intervening fourth sequence comprises a first polypeptide expression sequence and a second polypeptide expression sequence, wherein said first polypeptide expression sequence includes:

(i) a first transcriptional promoter;

(ii) a first gene which is native or foreign to the expression vector, said first gene being under the control of said first transcriptional promoter; and (iii) a first transcriptional termination site;

and wherein said second polypeptide expression sequence includes:

(i) a second transcriptional promoter;

(ii) a second gene which is native or foreign to the expression vector, said second gene being under the control of said second transcriptional promoter; and (iii) a second transcriptional termination site.

2. The plasmid replicon according to claim 1 wherein the first and second polypeptide expression sequences are arranged in the opposite sense to one another on separate strands of the DNA.

3. The plasmid replicon according to claim 1 wherein the first and second polypeptide expression sequences are arranged in the same sense on the same strand of DNA.

4. The plasmid replicon according to claim 1 wherein a selectable gene or an essential functional gene for the expression vector is located between the two polypeptide expression sequences.

5. The plasmid replicon of claim 4 wherein said first and second polypeptide expression sequences are arranged in the opposite sense to one another on separate strands of the DNA.

6. The plasmid replicon according to claim 1 wherein each polypeptide expression sequence includes a different unique restriction site for introduction of a gene which is native or foreign to the expression vector.

7. The plasmid replicon according to claim 1 including a plurality of pairs of said first and second polypeptide expression sequences.

8. The plasmid replicon according to claim 1 wherein said expression vector transfects a susceptible insect or insect cell.

9. The plasmid replicon according to claim 1 wherein one of said polypeptide expression sequences includes a structural gene which codes for a protein selected from the group consisting of AcNPV polyhedrin protein, hepatitis B surface antigen and hepatitis B core antigen.

10. A plasmid replicon for use in introducing a plurality of genes into an expression vector, said plasmid replicon comprising double-stranded DNA containing the following sequences:
   a) a first sequence allowing the replicon to be reproduced in a bacterial host;
   b) a second sequence adapted to permit an intervening sequence located between said second sequence and a third sequence of (c) to be introduced into an expression vector;
   c) a third sequence adapted to permit an intervening sequence located between said second sequence of (b) and said third sequence to be introduced into an expression vector; and
   d) a fourth sequence which is an intervening sequence located between said second sequence of (b) and said third sequence of (c), wherein said intervening fourth sequence comprises a first polypeptide expression sequence and a second polypeptide expression sequence,
      wherein said first polypeptide expression sequence includes:
         (i) a first transcriptional promoter;
         (ii) a first unique restriction site for introduction of a first gene which is native or foreign to the expression vector, said first gene being under the control of said first transcriptional promoter; and
         (iii) a first transcriptional termination site;
      and wherein said second polypeptide expression sequence includes:
         (i) a second transcriptional promoter;
         (ii) a second unique restriction site for introduction of a second gene which is native or foreign to the expression vector, said second gene being under the control of said second transcriptional promoter; and
         (iii) a second transcriptional termination site.

11. A sequence cassette for use in constructing a plasmid replicon as in claim 10, wherein said sequence cassette comprises double-stranded DNA containing a first and a second polypeptide expression sequence, wherein said first polypeptide expression sequence includes:
   (i) a first transcriptional promoter;
   (ii) a first unique restriction site for introduction of a first gene which is native or foreign to the expression vector, said first gene being under the control of said first transcriptional promoter;
   (iii) a first transcriptional termination site;
wherein said second polypeptide expression sequence includes:
   (i) a second transcriptional promoter;
   (ii) a second unique restriction site for introduction of a second gene which is native or foreign to the expression vector, said second gene being under the control of said second transcriptional promoter;
   (iii) a second transcriptional termination site,
and wherein said first and second polypeptide expression sequences are flanked by flanking sequences which are homologous with sequences of an expression vector, such that when recombined in to the vector, no essential genes of the expression vector are lost.

12. The sequence cassette according to claim 11 wherein said flanking sequences are arranged to allow the intervening sequences to be introduced without loss of vector DNA sequences.

13. The sequence cassette according to claim 11 wherein said flanking sequences are arranged to allow the intervening sequences to be introduced with replacement of nonessential vector DNA sequences.

14. The sequence cassette according to claim 11 wherein said flanking sequences are arranged to allow the intervening sequences to be introduced to replace intergenic or non-regulatory regions of the expression vector.

15. A set of sequence cassettes, each according to claim 11, wherein the homologous sequences of each cassette of the set are homologous to different regions of the vector genome, allowing a plurality of pairs of polypeptide expression sequences to be introduced into the vector genome, with each pair being located at a separate location.

16. The sequence cassette of claim 11 wherein said first and second polypeptide expression sequences are arranged in the opposite sense to one another on separate strands of DNA.

17. The sequence cassette of claim 11 wherein said first and second polypeptide expression sequences are arranged in the same sense on the same strand of DNA.

18. The sequence cassette of claim 11 wherein a selectable gene or an essential functional gene for the expression vector is located between the two polypeptide expression sequences.

19. A viral expression vector, suitable for transfecting an insect cell and having an insert adapted to direct synthesis in the cell of at least one polypeptide not normally encoded by the nuclear DNA of the cell, said insert comprising double stranded DNA containing a sequence which comprises a first and a second polypeptide expression sequence, wherein said first polypeptide expression sequence includes:
   (i) a first transcriptional promoter;
   (ii) a first gene which is native or foreign to the expression vector, said first gene being under the control of said first transcriptional promoter; and
   (iii) a first transcriptional termination site;
and wherein said second polypeptide expression sequence includes:
   (i) a second transcriptional promoter;
   (ii) a second gene which is native or foreign to the expression vector, said second gene being under the control of said second transcriptional promoter; and
   (iii) a second transcriptional termination site.

20. A viral expression vector according to claim 19 produced by first introducing a sequence cassette into a plasmid replicon for use in introducing a plurality of genes into the expression vector, wherein the plasmid replicon comprises (a) one or more sequences allowing the replicon to be produced in a bacterial host;

(b) a second sequence adapted to permit an intervening sequence located between said second sequence and a third sequence of (c) to be introduced into the expression vector;

(c) a third sequence adapted to permit an intervening sequence located between said second sequence of (b) and said third sequence to be introduced into the expression vector; and (d) a fourth sequence which is an intervening sequence located between said second sequence of (b) and third sequence of (c), wherein said intervening fourth sequence comprises a first polypeptide expression sequence and a second polypeptide expression sequence, wherein said first polypeptide expression sequence includes:
(i) a transcriptional promoter;
(ii) a unique restriction site for introduction of a gene which is native or foreign to the expression vector; and
(iii) a transcription termination site;

wherein said second polypeptide expression sequence includes:
(i) a transcriptional promoter;
(ii) a unique restriction site for introduction of a gene which is native or foreign to the expression vector; and
(iii) a transcription termination site;

and wherein said first and second polypeptide expression sequences are both flanked by sequences which are homologous with the sequences of the expression vector, such that when recombined in to the vector, no essential functional genes of the expression vector are lost.

21. An expression vector according to claim 19, produced by first introducing a sequence cassette into a plasmid replicon in constructing a plasmid replicon for use in introducing a plurality of genes into the expression vector, wherein the plasmid replicon comprises (a) one or more sequences allowing the replicon to be produced in a bacterial host;

(b) a second sequence adapted to permit an intervening sequences located between said second sequence and a third sequence of (c) to be introduced into the expression vector;

(c) a third sequence adapted to permit an intervening sequence located between said second sequence of (b) and said third sequence to be introduced into the expression vector;

(d) a fourth sequence which is an intervening sequence located between said second sequence of (b) and said third sequence of (c), wherein said intervening fourth sequence comprises a first polypeptide expression sequence and a second polypeptide expression sequence, wherein said first polypeptidc expression sequence includes:
(i) a transcriptional promoter;
(ii) a unique restriction site for introduction of a gene which is native or foreign to the expression vector; and
(iii) a transcription termination site;

wherein said second polypeptide expression sequence includes:
(i) a transcriptional promoter;
(ii) a unique restriction site for introduction of a gene which is native or foreign to the expression vector; and
(iii) a transcription termination site;

and wherein the homologous regions of each cassette of the set are homologous to different regions of the vector genome, allowing a plurality of pairs of polypeptide expression sequences to be introduced into the vector genome, with each pair being located at a separate location.

22. The viral expression vector according to claim 19 further defined to contain a structural gene which codes for a viral protein normally expressed during infection of insect cells by wild type virus.

23. The viral expression vector according to claim 19 wherein at least one of said promoters is a promoter for a viral protein normally expressed during infection of insect cells by wild type virus.

24. The viral expression vector according to claim 23 wherein the wild type virus is a baculovirus.

25. The viral expression vector according to claim 19 wherein at least one of said promoters is the promoter for the polyhedrin gene of *Autographa californica* nuclear polyhedrosis virus.

26. The viral expression vector according to claim 19 wherein one of said polypeptide expression sequences includes a structural gene which codes for a protein selected from the group consisting of AcNPV polyhedrin protein, hepatitis B surface antigen, and hepatitis B core antigen.

27. A method of constructing a viral expression vector suitable for transfecting an insect cell, which comprises using the plasmid replicon of claim 1 to introduce an insert into a recipient vector lacking said insert, wherein the resulting viral expression vector has an insert adapted for the direct synthesis in the cell of at least one polypeptide not normally encoded by the nuclear DNA of the cell, said insert comprising double-stranded DNA having an intervening sequence located between first and second sequences, said intervening sequence comprising a first polypeptide expression sequence and a second polypeptide expression sequence, wherein each polypeptide expression sequence includes:

(i) a transcriptional promoter;
(ii) a gene which is native or foreign to the expression vector;
(iii) a transcriptional termination site.

28. A process of producing one or more desired polypeptides, which comprises:

a infecting susceptible insects or insect cells with a viral expression vector suitable for transfecting an insect cell and having an insert adapted to direct the synthesis in the cell of at least one polypeptide not normally encoded by the nuclear DNA of the cell, said insert comprising double-stranded DNA containing a sequence which comprises a first polypeptide expression sequence and a second polypeptide expression sequence, wherein said first polypeptide expression sequence includes:
(i) a first transcriptional promoter;
(ii) a first gene which is native or foreign to the expression vector said first gene being under the control of said a first transcriptional promoter; and
(iii) a first transcriptional termination site;

and wherein said second polypeptide expression sequence includes:
  (i) a second transcriptional promoter;
  (ii) a second gene which is native or foreign to the expression vector said second gene being under the control of said a second transcriptional promoter; and
  (iii) a second transcriptional termination site; and
(b) recovering the desired polypeptide or polypeptides from the infected susceptible insects or insect cells.

29. The process according to claim 28 wherein the individual susceptible insects are caterpillars.

* * * * *